(12) United States Patent
Hinton et al.

(10) Patent No.: US 7,320,790 B2
(45) Date of Patent: Jan. 22, 2008

(54) HUMANIZED ANTIBODIES

(75) Inventors: Paul Robert Hinton, Sunnyvale, CA (US); Maximiliano J. Vasquez, Palo Alto, CA (US)

(73) Assignee: Eli Lilly and Company, Indianapolis, IN (US)

( * ) Notice: Subject to any disclaimer, the term of this patent is extended or adjusted under 35 U.S.C. 154(b) by 473 days.

(21) Appl. No.: 10/497,475

(22) PCT Filed: Apr. 26, 2002

(86) PCT No.: PCT/US02/11854

§ 371 (c)(1),
(2), (4) Date: Jan. 10, 2005

(87) PCT Pub. No.: WO02/088307

PCT Pub. Date: Nov. 7, 2002

(65) Prior Publication Data

US 2005/0142131 A1    Jun. 30, 2005

Related U.S. Application Data

(60) Provisional application No. 60/287,653, filed on Apr. 30, 2001.

(51) Int. Cl.
*A61K 39/395* (2006.01)
*C12P 21/08* (2006.01)
*C07K 16/18* (2006.01)
*C07H 21/04* (2006.01)
*C12N 5/16* (2006.01)

(52) U.S. Cl. .............. 424/133.1; 530/387.3; 530/387.9; 536/23.53; 435/328; 435/331; 424/139.1; 424/141.1

(58) Field of Classification Search .............. None
See application file for complete search history.

(56) References Cited

U.S. PATENT DOCUMENTS

| | | | |
|---|---|---|---|
| 5,441,870 A | | 8/1995 | Seubert et al. |
| 5,530,101 A | | 6/1996 | Queen et al. |
| 5,538,845 A | | 7/1996 | Knops et al. |
| 5,585,089 A | | 12/1996 | Queen et al. |
| 5,589,154 A | * | 12/1996 | Anderson .............. 424/1.41 |
| 5,593,846 A | | 1/1997 | Schenk et al. |
| 5,604,102 A | | 2/1997 | McConlogue et al. |
| 5,605,811 A | | 2/1997 | Seubert et al. |
| 5,688,651 A | | 11/1997 | Solomon |
| 5,693,761 A | | 12/1997 | Queen et al. |
| 5,693,762 A | | 12/1997 | Queen et al. |
| 6,175,057 B1 | | 1/2001 | Mucke et al. |
| 6,180,370 B1 | | 1/2001 | Queen et al. |
| 2003/0165496 A1 | | 9/2003 | Basi et al. |

FOREIGN PATENT DOCUMENTS

| | | |
|---|---|---|
| EP | 613 007 | 8/1994 |
| WO | WO 96/18900 | 6/1996 |
| WO | WO 96/25435 | 8/1996 |
| WO | WO 98/44955 | 10/1998 |
| WO | WO 99/06066 | 2/1999 |
| WO | WO 99/27944 | 6/1999 |
| WO | WO 99/60024 | 11/1999 |
| WO | WO 00/72876 A2 | 12/2000 |
| WO | WO 00/72880 A2 | 12/2000 |
| WO | WO 00/77178 | 12/2000 |
| WO | WO 01/18169 | 3/2001 |
| WO | WO 02/46237 A2 | 6/2002 |

OTHER PUBLICATIONS

De Felice FG and Ferreira ST. beta-Amyloid production, aggregation, and clearance as targets for therapy in Alzheimer's disease. Cell Mol Neurobiol. 2002; 22(5-6): 545-563.*
De Lustig ES et al. Peripheral markers and diagnostic criteria in Alzheimer's disease: Critical evaluations. Rev in Neurosciences, 1994; 5: 213-224.*
Hartman RE et al. Treatment with an amyloid-beta antibody ameliorates plaque load, learning deficits, and hippocampal long-term potentiation in a mouse model of Alzheimer's disease. J Neurosci, 2005; 25(26): 6213-6220.*
Johnson-Wood K et al. Amyloid precursor protein processing and Abeta42 deposition in a transgenic mouse model of Alzheimer disease. Proc Natl Acad Sci USA, 1997, 94: 1550-1555.*
Kimchi EY et al. Analysis of cerebral amyloid angiopathy in a transgenic mouse model of Alzheimer disease using in vivo multiphoton microscopy. J. Neuropathol Exp Neurol, 2001; 60(3): 274-279.*
Münch G and Robinson SR. Potential neurotoxic inflammatory response to Abeta vaccination in humans. J Neural Transm, 2002; 109: 1081-1087.*
Small GW et al. Cerebral metabolic and cognitive decline in persons at genetic risk for Alzheimer's disease. Proc Natl Acad Sci USA, 2000; 97:6037-6042.*
Vickers JC. A vaccine against Alzheimer's disease, developments to date. Drugs Aging, 2002, 19(7): 487-494.*
Jones, PT, et al., "Replacing the complementarity-determining regions in a human antibody with those from a mouse," Nature, vol. 321, pp. 522-525, May 29, 1986.
Frenkel, D, et al, "N-terminal EFRH sequence of Alzheimer's β-amyloid peptide represents the epitope of its anti-aggregating antibodies," J. Neuroimmunol., vol. 88, No. 1-2, pp. 85-90, Aug. 1, 1998.

(Continued)

*Primary Examiner*—Elizabeth C. Kemmerer
*Assistant Examiner*—Kimberly A. Ballard
(74) *Attorney, Agent, or Firm*—Mark J. Stewart; James J. Kelley

(57) ABSTRACT

Humanized forms of mouse antibody 10D5 that retain the binding properties of mouse 10D5 are disclosed. Also disclosed are processes for making the humanized antibody, intermediates for making the humanized antibodies, including, nucleotide sequences, vectors, transformed host cells, and methods of using the humanized antibody to treat, prevent, alleviate, reverse, or otherwise ameliorate symptoms or pathology or both, that are associated with Down's syndrome or pre-clinical or clinical Alzheimer's disease or cerebral amyloid angiopathy.

17 Claims, No Drawings

OTHER PUBLICATIONS

Frenkel, D, et al., "High affinity binding of monoclonal antibodies to the sequential epitope EFRH of β-amyloid peptide is essential for modulation of fibrillar aggregation," J. Neuroimmunol., vol. 95, No. 1-2, pp. 136-142, Mar. 1, 1999.

Parvizi J, et al., "The Selective Vulnerability of Brainstem Nuclei to Alzheimer's Disease," Ann Neurol., vol. 49, No. 1, pp. 53-66, Jan. 2001.

Seubert, P, et al., "Isolation and quantification of soluble Alzheimer's β-peptide from biological fluids," Nature, vol. 359, pp. 325-327, 1992.

Van Gool, WA, et al., "Concentrations of amyloid-β protein in cerebrospinal fluid increases with age in patients free from neurodegenerative disease," Neuroscience Lett., vol. 172, pp. 122-124, 1994.

Tabaton, M, el al., "Soluble Amyloid β-Protein is a Marker of Alzheimer Amyloid in Brain but Not in Cerebrospinal Fluid," Biochemical and Biophysical Research Communications, vol. 200, No. 3, pp. 1598-1603, May 16, 1994.

Walker, L, et al., "Labeling of Cerebral Amyloid In Vivo with a Monoclonal Antibody," J Neuropathol Exp Neurol., vol. 53, No. 4, pp. 377-383, Jul. 1994.

Nitsch, RM, et al., "Cerebrospinal Fluid Levels of Amyloid β-Protein in Alzheimer's Disease: Inverse Correlation with Severity of Dementia and Efect of Apolipoprotein E Genotype," Annals Neurology, vol. 37, pp. 512-518, 1995.

Gomez-Isla, T, et al., A Novel Presenilin-1 Mutation: Increased β-Amyloid and Neurofibrillary Changes, Annals Neurology, vol. 41, pp. 809-813, 1997.

Schenk, D, et al., "Immunization with amyloid-β attenuates Alzheimer-disease-like pathology in the PDAPP mouse," Nature, vol. 400, pp. 173-177, 1999.

Bard, F, et al., "Antibodies against Abeta reduce Amyloid Burden In Vivo," Society for Neuroscience Abstracts, vol. p. 1059, Nov. 4, 2000.

Bard, F, et al., "Peripherally administered antibodies against amyloid beta-peptide enter the central nervous system and reduce pathology in a mouse model of Alzheimer disease," Nature Med., vol. 6, No. 8, pp. 916-919, 2000.

Chothia, C, et al., "Canonical Structures for the Hypervariable Regions of Immunoglobulins,", J. Mol. Biol, vol. 196, pp. 901-917, 1987.

Chothia, C, et al., et al., "Conformations of imunoglobulin hypervariable regions,", Nature, vol. 342, pp. 878-883, Dec. 21-28, 1989.

Queen, et al., "A humanized antibody that binds to the interleukin 2 receptor," Proc. Natl. Acad. Sci. USA, vol. 86, pp. 10029-10033, Dec. 1989.

Co, MS, et al., "Humanized antibodies for antiviral therapy," Proc. Natl. Acad. Sci. USA, vol. 88, pp. 2869, Apr. 1991.

Remington's Pharmaceutical Sciences, 18th Edition, Mack Publishing Co., Easton PA, pp. 1481-1498, 1504-1512, and 1519-1580, 1990.

Hyman, B., et al., "Kunitz Protease Inhibitor-Containing Amyloid β Protein Precursor Immunoreactivity in Alzheimer's disease," J. Neuropath. Exp. Neurol., vol. 51, No. 1, pp. 76-83, Jan. 1992.

Walker, L, et al., "Labeling of β-Amyloid In Vivo," (Abstract) Neurobiol. Aging, vol. 13, Supl. 1, S23, 1992.

Hanan, E, et al., "Inhibitory Effect of Monoclonal Antibodies on Alzheimer's β-Amyloid Peptide Aggregation" Int. J. Exp. Clin. Invest., vol. 3, pp. 130-133, 1996.

Solomon, B, et al., "Monoclonal antibodies inhibit n vitro fibrillar aggregation of the Alzheimer beta-amyloid peptide," Proc Natl Acad Sci U S A., vol. 93, No. 1, pp. 452-455, Jan. 1996.

Friedland, RP, et al., "Neuroimaging of Vessel Amyloid in Alzheimer's Disease," Ann. NY Acad. Science, 826, pp. 242-247, 1997.

Goldman, DL, et al., "Pharmacokinetics and Biodistribution of a Monoclonal Antibody to Cryptococcus Neoformans Capsular Polysaccharide Antigen . . . ," Journal of Medical & Veterinary Mycology, vol. 35, pp. 271-278, 1997.

Solomon, B, et al., "Disaggregation of Alzheimer β-amyloid by site-directed mAb," Proc. Natl. Acad. Sci.,, vol. 94, pp. 4109-4112, 1997.

St. George-Hyslop, P, et al., "Antibody clears senile plaques," Nature, vol. 400, pp. 116-117, Jul. 8, 1999.

Blass, JP, "Immunologic Treatment of Alzheimer's Disease," New Engl. J. Med. vol. 341, No. 22, pp. 1694-1695, Nov. 25, 1999.

Schenk, D, et al., "A possible vaccine for treatment of AD," World Alzheimer's Congress 2000, Plenary Session III, 605, Washington, D.C., Jul. 11, 2000.

Bacskai BJ, et al., "Imaging of amyloid-â deposits in brains of living mice permits direct observation of clearance of plaques with immunotherapy," Nature Medicine vol. 7, No. 3, pp. 369-372, Mar. 2001.

Simmons, L, et al., "Secondary Structure of Amyloid β Peptide Correlates with Neurotoxic Activity In Vitro," Molecular Pharmacology, vol. 45, pp. 373-379, 1994.

Arendash, GW, et al., "Behavioral Assessment of Alzheimer's Transgenic Mice Following Long-Term Aβ Vaccination: Task Specificity and Correlations between Aβ Deposition and Spatial Memory," DNA and Cell Biology, vol. 20, No. 11, pp. 737-744, 2001.

DeMattos, RB, et al, "Peripheral anti-Aβ antibody alters CNS and plasma Aβ clearance and decreases brain Aβ burden in a mouse model of Alzheimer's disease," PNAS, vol. 98, No. 15, pp. 8850-8855, 2001.

Dickey, CA, et al., "Duration and Specificity of Humoral Immune Responses in Mice Vaccinated with the Alzheimer's Disease-Associated β-Amyloid 1-42 Peptide," DNA and Cell Biology, vol. 20, No. 11, pp. 723-729, 2001.

Esiri, MM, et al, "Is an effective immune intervention for Alzheimer's disease in prospect?" Trends Pharmacol Sci,, vol. 22, No. 1, pp. 2-3, 2001.

Haass C, et al, "Protofibrils, the unifying toxic molecule of neurodegenerative disorders?" Nature Neurosciences, vol. 4, No. 9, pp. 219-224, Sep. 2001.

Ruker, F, et al., "Expression of a Human Monoclonal Anti-HIV-1 Antibody in CHO Cells," Ann. N.Y. Acad. Sci., vol. 646, pp. 212-219, Dec. 27, 1991.

Masliah E, et al., "Comparison of Neurodegenerative Pathology in Transgenic Mice Overexpressing V717F β-Amyloid Precursor Protein and Alzheimer's Disease," J. Neurosci., vol. 16, No. 18, pp. 5795-5811, Sep. 15, 1996.

Vanderstichele H, et al., "Development of a Specific Diagnostic Test for Measurement of β-Amyloid (1-42) [βA4(1-42)] in CSF," Adv. Behav. Biol., pp. 773-778 (1998).

\* cited by examiner

SEQUENCE LISTING

<160> NUMBER OF SEQ ID NOS: 20

<210> SEQ ID NO 1
<211> LENGTH: 16
<212> TYPE: PRT
<213> ORGANISM: mus sp.

<400> SEQUENCE: 1

Arg Ser Ser Gln Asn Ile Ile His Ser Asn Gly Asn Thr Tyr Leu Glu
1               5                   10                  15

<210> SEQ ID NO 2
<211> LENGTH: 7
<212> TYPE: PRT
<213> ORGANISM: mus sp.

<400> SEQUENCE: 2

Lys Val Ser Asn Arg Phe Ser
1               5

<210> SEQ ID NO 3
<211> LENGTH: 9
<212> TYPE: PRT
<213> ORGANISM: Mus sp.

<400> SEQUENCE: 3

Phe Gln Gly Ser His Val Pro Leu Thr
1               5

<210> SEQ ID NO 4
<211> LENGTH: 7
<212> TYPE: PRT
<213> ORGANISM: Mus sp.

<400> SEQUENCE: 4

Thr Ser Gly Met Gly Val Ser
1               5

<210> SEQ ID NO 5
<211> LENGTH: 16
<212> TYPE: PRT
<213> ORGANISM: Mus sp.

<400> SEQUENCE: 5

His Ile Tyr Trp Asp Asp Asp Lys Arg Tyr Asn Pro Ser Leu Lys Ser
1               5                   10                  15

<210> SEQ ID NO 6
<211> LENGTH: 13
<212> TYPE: PRT
<213> ORGANISM: Mus sp.

<400> SEQUENCE: 6

Arg Pro Ile Thr Pro Val Leu Val Asp Ala Met Asp Tyr
1               5                   10

<210> SEQ ID NO 7
<211> LENGTH: 113
<212> TYPE: PRT
<213> ORGANISM: humanized antibody
<220> FEATURE:
<221> NAME/KEY: MISC_FEATURE
<222> LOCATION: (3)..(3)
<223> OTHER INFORMATION: Xaa=Val or Leu

```
<220> FEATURE:
<221> NAME/KEY: MISC_FEATURE
<222> LOCATION: (7)..(7)
<223> OTHER INFORMATION: Xaa=Ser of Thr
<220> FEATURE:
<221> NAME/KEY: MISC_FEATURE
<222> LOCATION: (14)..(14)
<223> OTHER INFORMATION: Xaa=Thr or Ser
<220> FEATURE:
<221> NAME/KEY: MISC_FEATURE
<222> LOCATION: (17)..(17)
<223> OTHER INFORMATION: Xaa=Gln, Asp, or Asn
<220> FEATURE:
<221> NAME/KEY: MISC_FEATURE
<222> LOCATION: (30)..(30)
<223> OTHER INFORMATION: Xaa=Ile or Val
<220> FEATURE:
<221> NAME/KEY: MISC_FEATURE
<222> LOCATION: (50)..(50)
<223> OTHER INFORMATION: Xaa=Arg or Lys
<220> FEATURE:
<221> NAME/KEY: MISC_FEATURE
<222> LOCATION: (88)..(88)
<223> OTHER INFORMATION: Xaa=Val or Leu
<220> FEATURE:
<221> NAME/KEY: MISC_FEATURE
<222> LOCATION: (105)..(105)
<223> OTHER INFORMATION: Xaa=Gly or Ala
<220> FEATURE:
<221> NAME/KEY: MISC_FEATURE
<222> LOCATION: (109)..(109)
<223> OTHER INFORMATION: Xaa=Val or Leu

<400> SEQUENCE: 7

Asp Val Xaa Met Thr Gln Xaa Pro Leu Ser Leu Pro Val Xaa Leu Gly
1               5                   10                  15

Xaa Pro Ala Ser Ile Ser Cys Arg Ser Ser Gln Asn Ile Xaa His Ser
            20                  25                  30

Asn Gly Asn Thr Tyr Leu Glu Trp Tyr Leu Gln Lys Pro Gly Gln Ser
        35                  40                  45

Pro Xaa Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Phe Gln Gly
                85                  90                  95

Ser His Val Pro Leu Thr Phe Gly Xaa Gly Thr Lys Xaa Glu Ile Lys
            100                 105                 110

Arg

<210> SEQ ID NO 8
<211> LENGTH: 123
<212> TYPE: PRT
<213> ORGANISM: humanized antibody
<220> FEATURE:
<221> NAME/KEY: MISC_FEATURE
<222> LOCATION: (1)..(1)
<223> OTHER INFORMATION: Xaa=Gln or Glu
<220> FEATURE:
<221> NAME/KEY: MISC_FEATURE
<222> LOCATION: (2)..(2)
<223> OTHER INFORMATION: Xaa=Val or Ala
<220> FEATURE:
<221> NAME/KEY: MISC_FEATURE
<222> LOCATION: (64)..(64)
<223> OTHER INFORMATION: Xaa=Ser or Thr
<220> FEATURE:
<221> NAME/KEY: MISC_FEATURE
<222> LOCATION: (77)..(77)
<223> OTHER INFORMATION: Xaa=Lys or Arg
```

```
<220> FEATURE:
<221> NAME/KEY: MISC_FEATURE
<222> LOCATION: (78)..(78)
<223> OTHER INFORMATION: Xaa=Ser or Thr
<220> FEATURE:
<221> NAME/KEY: MISC_FEATURE
<222> LOCATION: (83)..(83)
<223> OTHER INFORMATION: Xaa=Thr or Ser
<220> FEATURE:
<221> NAME/KEY: MISC_FEATURE
<222> LOCATION: (84)..(84)
<223> OTHER INFORMATION: Xaa=Met, Ile or Leu
<220> FEATURE:
<221> NAME/KEY: MISC_FEATURE
<222> LOCATION: (86)..(86)
<223> OTHER INFORMATION: Xaa=Asn, Ser, Thr
<220> FEATURE:
<221> NAME/KEY: MISC_FEATURE
<222> LOCATION: (87)..(87)
<223> OTHER INFORMATION: Xaa=Met, Val, or Leu
<220> FEATURE:
<221> NAME/KEY: MISC_FEATURE
<222> LOCATION: (118)..(118)
<223> OTHER INFORMATION: Xaa=Leu or Ser

<400> SEQUENCE: 8

Xaa Xaa Thr Leu Lys Glu Ser Gly Pro Val Leu Val Lys Pro Thr Glu
 1               5                  10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Xaa
    50                  55                  60

Leu Lys Ser Arg Leu Thr Ile Ser Lys Asp Thr Ser Xaa Xaa Gln Val
65                  70                  75                  80

Val Leu Xaa Xaa Thr Xaa Xaa Asp Pro Val Asp Thr Ala Thr Tyr Tyr
            85                  90                  95

Cys Val Arg Arg Pro Ile Thr Pro Val Leu Val Asp Ala Met Asp Tyr
            100                 105                 110

Trp Gly Gln Gly Thr Xaa Val Thr Val Ser Ser
        115                 120

<210> SEQ ID NO 9
<211> LENGTH: 113
<212> TYPE: PRT
<213> ORGANISM: humanized antibody

<400> SEQUENCE: 9

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Asn Ile Ile His Ser
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
            85                  90                  95

Ser His Val Pro Leu Thr Phe Gly Gly Gly Thr Lys Val Glu Ile Lys
            100                 105                 110
```

Arg

<210> SEQ ID NO 10
<211> LENGTH: 123
<212> TYPE: PRT
<213> ORGANISM: humanized antibody

<400> SEQUENCE: 10

```
Gln Val Thr Leu Lys Glu Ser Gly Pro Val Leu Val Lys Pro Thr Glu
1               5                   10                  15
Thr Leu Thr Leu Thr Cys Thr Phe Ser Gly Phe Ser Leu Ser Thr Ser
            20                  25                  30
Gly Met Gly Val Ser Trp Ile Arg Gln Pro Pro Gly Lys Ala Leu Glu
        35                  40                  45
Trp Leu Ala His Ile Tyr Trp Asp Asp Lys Arg Tyr Asn Pro Ser
    50                  55                  60
Leu Lys Ser Arg Leu Thr Ile Ser Lys Asp Thr Ser Lys Ser Gln Val
65                  70                  75                  80
Val Leu Thr Met Thr Asn Met Asp Pro Val Asp Thr Ala Thr Tyr Tyr
                85                  90                  95
Cys Val Arg Arg Pro Ile Thr Pro Val Leu Val Asp Ala Met Asp Tyr
            100                 105                 110
Trp Gly Gln Gly Thr Leu Val Thr Val Ser Ser
        115                 120
```

<210> SEQ ID NO 11
<211> LENGTH: 219
<212> TYPE: PRT
<213> ORGANISM: humanized antibody

<400> SEQUENCE: 11

```
Asp Val Val Met Thr Gln Ser Pro Leu Ser Leu Pro Val Thr Leu Gly
1               5                   10                  15
Gln Pro Ala Ser Ile Ser Cys Arg Ser Ser Gln Asn Ile Ile His Ser
            20                  25                  30
Asn Gly Asn Thr Tyr Leu Glu Trp Tyr Leu Gln Lys Pro Gly Gln Ser
        35                  40                  45
Pro Arg Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Ser His Val Pro Leu Thr Phe Gly Gly Gly Thr Lys Val Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
            195                 200                 205
Pro Val Thr Lys Ser Phe Asn Arg Gly Glu Cys
            210                 215

<210> SEQ ID NO 12
<211> LENGTH: 453
<212> TYPE: PRT
<213> ORGANISM: humanized antibody

<400> SEQUENCE: 12

Gln Val Thr Leu Lys Glu Ser Gly Pro Val Leu Val Lys Pro Thr Glu
  1               5                  10                  15

Thr Leu Thr Leu Thr Cys Thr Phe Ser Gly Phe Ser Leu Ser Thr Ser
                 20                  25                  30

Gly Met Gly Val Ser Trp Ile Arg Gln Pro Pro Gly Lys Ala Leu Glu
             35                  40                  45

Trp Leu Ala His Ile Tyr Trp Asp Asp Asp Lys Arg Tyr Asn Pro Ser
     50                  55                  60

Leu Lys Ser Arg Leu Thr Ile Ser Lys Asp Thr Ser Lys Ser Gln Val
 65                  70                  75                  80

Val Leu Thr Met Thr Asn Met Asp Pro Val Asp Thr Ala Thr Tyr Tyr
                 85                  90                  95

Cys Val Arg Arg Pro Ile Thr Pro Val Leu Val Asp Ala Met Asp Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350
```

```
Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 13
<211> LENGTH: 46
<212> TYPE: DNA
<213> ORGANISM: DNA primer

<400> SEQUENCE: 13

```
tatagagctc aagcttggat ggtgggaaga tggatacagt tggtgc          46
```

<210> SEQ ID NO 14
<211> LENGTH: 50
<212> TYPE: DNA
<213> ORGANISM: DNA primer

<400> SEQUENCE: 14

```
tatagagctc aagcttccag tggatagach gatggggstg tygttttggc      50
```

<210> SEQ ID NO 15
<211> LENGTH: 1953
<212> TYPE: DNA
<213> ORGANISM: humanized antibody

<400> SEQUENCE: 15

```
acgcgtccac catgaagttg cctgttaggc tgttggtact gatgttctgg attcctgctt    60
ccagcagtga tgttgtgatg acccaatctc cactctccct gcctgtcact cttggacagc   120
cagcctccat ctcttgcaga tctagtcaga acattataca tagtaatgga aacacctatt   180
tagaatggta cctgcagaaa ccaggccagt ctccaaggct cctgatctac aaagtttcca   240
accgattttc tggggtccca gacaggttca gtggcagtgg atcagggaca gatttcacac   300
tcaagatcag cagagtggag gctgaggatg tgggagttta ttactgcttt caaggttcac   360
atgttccgct cactttcggc ggagggacca aggtggaaat aaaacgtaag tgcactttcc   420
taatctagaa attctaaact ctgaggggt cggatgacg ggccattctt tgcctaaagc   480
attgagttta ctgcaaggtc agaaaagcat gcaagccct cagaatggct gcaaagagct   540
ccaacaaaac aatttagaac tttattaagg aataggggga agctaggaag aaactcaaaa   600
catcaagatt ttaaatacgc ttcttggtct ccttgctata attatctggg ataagcatgc   660
tgttttctgt ctgtccctaa catgccctgt gattatccgc aaacaacaca cccaagggca   720
gaactttgtt acttaaacac catcctgttt gcttcttcc tcaggaactg tggctgcacc   780
atctgtcttc atcttcccgc catctgatga gcagttgaaa tctggaactg cctctgttgt   840
gtgcctgctg aataacttct atcccagaga ggccaaagta cagtggaagg tggataacgc   900
```

-continued

| | |
|---|---|
| cctccaatcg ggtaactccc aggagagtgt cacagagcag gacagcaagg acagcaccta | 960 |
| cagcctcagc agcaccctga cgctgagcaa agcagactac gagaaacaca agtctacgc | 1020 |
| ctgcgaagtc acccatcagg gcctgagctc gcccgtcaca aagagcttca caggggaga | 1080 |
| gtgttagagg gagaagtgcc cccacctgct cctcagttcc agcctgaccc cctcccatcc | 1140 |
| tttggcctct gacccttttt ccacagggga cctacccta ttgcggtcct ccagctcatc | 1200 |
| tttcacctca ccccctcct cctccttggc tttaattatg ctaatgttgg aggagaatga | 1260 |
| ataaataaag tgaatctttg cacctgtggt ttctctcttt cctcatttaa taattattat | 1320 |
| ctgttgtttt accaactact caatttctct tataagggac taaatatgta gtcatcctaa | 1380 |
| ggcgcataac catttataaa aatcatcctt cattctattt taccctatca tcctctgcaa | 1440 |
| gacagtcctc cctcaaaccc acaagccttc tgtcctcaca gtcccctggg ccatggtagg | 1500 |
| agagacttgc ttccttgttt tcccctcctc agcaagccct catagtcctt tttaagggtg | 1560 |
| acaggtctta cagtcatata tcctttgatt caattccctg agaatcaacc aaagcaaatt | 1620 |
| tttcaaaaga gaaacctgc tataaagaga atcattcatt gcaacatgat ataaataac | 1680 |
| aacacaataa aagcaattaa ataaacaaac aatagggaaa tgtttaagtt catcatggta | 1740 |
| cttagactta atggaatgtc atgccttatt tacattttta aacaggtact gagggactcc | 1800 |
| tgtctgccaa gggccgtatt gagtactttc cacaacctaa tttaatccac actatactgt | 1860 |
| gagattaaaa acattcatta aaatgttgca aaggttctat aaagctgaga gacaaatata | 1920 |
| ttctataact cagcaatccc acttctagga tcc | 1953 |

<210> SEQ ID NO 16
<211> LENGTH: 3256
<212> TYPE: DNA
<213> ORGANISM: humanized antibody

<400> SEQUENCE: 16

| | |
|---|---|
| acgcgtccac catggacagg cttacttcct cattcctgct gctgattgtc cctgcatatg | 60 |
| tcctgtccca ggttactctg aaagagtctg gccctgtact agtgaagccc accgagaccc | 120 |
| tcactctgac ttgtactttc tctgggtttt cactgagcac ttctggtatg ggagtgagct | 180 |
| ggattcgtca gcctccagga aaggctctgg agtggctggc acacatttac tgggatgatg | 240 |
| acaagcgcta taacccatcc ctgaagagcc ggctcacaat ctccaaggat acctccaaaa | 300 |
| gccaggtagt cctcacgatg accaatatgg accctgtaga tactgccaca tactactgtg | 360 |
| ttcgaaggcc cattactccg gtactagtcg atgctatgga ctactgggc aaggaaccc | 420 |
| tggtcaccgt ctcctcaggt gagtcctcac aacctctaga gctttctggg gcaggccagg | 480 |
| cctgaccttg gctttggggc agggaggggg ctaaggtgag gcaggtggcg ccagccaggt | 540 |
| gcacacccaa tgcccatgag cccagacact ggacgctgaa cctcgcggac agttaagaac | 600 |
| ccagggcct ctgcgccctg ggcccagctc tgtcccacac cgcggtcaca tggcaccacc | 660 |
| tctcttgcag cctccaccaa gggcccatcg gtcttccccc tggcaccctc ctccaagagc | 720 |
| acctctgggg gcacagcggc cctgggctgc ctggtcaagg actacttccc cgaaccggtg | 780 |
| acggtgtcgt ggaactcagg cgccctgacc agcggcgtgc acaccttccc ggctgtccta | 840 |
| cagtcctcag gactctactc cctcagcagc gtggtgaccg tgccctccag cagcttgggc | 900 |
| acccagacct acatctgcaa cgtgaatcac aagcccagca acaccaaggt ggacaagaaa | 960 |
| gttggtgaga ggccagcaca gggagggagg gtgtctgctg gaagccaggc tcagcgctcc | 1020 |

-continued

```
tgcctggacg catcccggct atgcagcccc agtccagggc agcaaggcag gccccgtctg   1080
cctcttcacc cggaggcctc tgcccgcccc actcatgctc agggagaggg tcttctggct   1140
ttttccccag gctctgggca ggcacaggct aggtgcccct aacccaggcc ctgcacacaa   1200
aggggcaggt gctgggctca gacctgccaa gagccatatc cggaggacc ctgcccctga    1260
cctaagccca ccccaaaggc caaactctcc actccctcag ctcggacacc ttctctcctc   1320
ccagattcca gtaactccca atcttctctc tgcagagccc aaatcttgtg acaaaactca   1380
cacatgccca ccgtgcccag gtaagccagc ccaggcctcg ccctccagct caaggcggga   1440
caggtgccct agagtagcct gcatccaggg acaggcccca gccgggtgct gacacgtcca   1500
cctccatctc ttcctcagca cctgaactcc tggggggacc gtcagtcttc ctcttccccc   1560
caaaacccca ggacaccctc atgatctccc ggacccctga ggtcacatgc gtggtggtgg   1620
acgtgagcca cgaagaccct gaggtcaagt tcaactggta cgtggacggc gtggaggtgc   1680
ataatgccaa gacaaagccg cgggaggagc agtacaacag cacgtaccgt gtggtcagcg   1740
tcctcaccgt cctgcaccag gactggctga atggcaagga gtacaagtgc aaggtctcca   1800
acaaagccct cccagccccc atcgagaaaa ccatctccaa agccaaaggt gggacccgtg   1860
gggtgcgagg gccacatgga cagaggccgg ctcggcccac cctctgccct gagagtgacc   1920
gctgtaccaa cctctgtccc tacagggcag ccccgagaac acaggtgta cccctgccc    1980
ccatcccggg atgagctgac caagaaccag gtcagcctga cctgcctggt caaaggcttc   2040
tatcccagcg acatcgccgt ggagtgggag agcaatgggc agccggagaa caactacaag   2100
accacgcctc ccgtgctgga ctccgacggc tccttcttcc tctacagcaa gctcaccgtg   2160
gacaagagca ggtggcagca ggggaacgtc ttctcatgct ccgtgatgca tgaggctctg   2220
cacaaccact acacgcagaa gagcctctcc ctgtctccgg gtaaatgagt gcgacggccg   2280
gcaagccccc gctccccggg ctctcgcggt cgcacgagga tgcttggcac gtaccccctg   2340
tacatacttc ccgggcgccc agcatggaaa taaagcaccc agcgctgccc tgggcccctg   2400
cgagactgtg atggttcttt ccacgggtca ggccgagtct gaggcctgag tggcatgagg   2460
gaggcagagc gggtcccact gtccccacac tggcccaggc tgtgcaggtg tgcctgggcc   2520
gcctagggtg gggctcagcc aggggctgcc ctcggcaggg tggggatttg ccagcgtgg   2580
ccctccctcc agcagcacct gccctgggct gggcacggg aagccctagg agccctggg    2640
gacagacaca cagcccctgc ctctgtagga gactgtcctg ttctgtgagc gccctgtcct   2700
ccgacctcca tgcccactcg ggggcatgcc tagtccatgt gcgtagggac aggccctccc   2760
tcacccatct accccacgg cactaacccc tggctgccct gcccagcctc gcacccgcat    2820
ggggacacaa ccgactccgg ggacatgcac tctcgggccc tgtggaggga ctggtgcaga   2880
tgcccacaca cacactcagc ccagacccgt tcaacaaacc ccgcactgag gttggccggc   2940
cacacggcca ccacacacac acgtgcacgc ctcacacacg gagcctcacc cgggcgaact   3000
gcacagcacc cagaccagag caaggtcctc gcacacgtga acactcctcg gacacaggcc   3060
cccacgagcc ccacgcggca cctcaaggcc cacgagcctc tcggcagctt ctccacatgc   3120
tgacctgctc agacaaaccc agccctcctc tcacaagggt gccctgcag ccgccacaca    3180
cacacagggg atcacacacc acgtcacgtc cctggccctg ccccacttcc cagtgccgcc   3240
cttccctgca ggatcc                                                   3256
```

<210> SEQ ID NO 17
<211> LENGTH: 714

<212> TYPE: DNA
<213> ORGANISM: humanized antibody

<400> SEQUENCE: 17

| | |
|---|---|
| atgaagttgc ctgttaggct gttggtactg atgttctgga ttcctgcttc cagcagtgat | 60 |
| gttgtgatga cccaatctcc actctccctg cctgtcactc ttggacagcc agcctccatc | 120 |
| tcttgcagat ctagtcagaa cattatacat agtaatggaa cacctatttt agaatggtac | 180 |
| ctgcagaaac caggccagtc tccaaggctc ctgatctaca agtttccaa ccgattttct | 240 |
| ggggtcccag acaggttcag tggcagtgga tcagggacag atttcacact caagatcagc | 300 |
| agagtggagg ctgaggatgt gggagtttat tactgctttc aaggttcaca tgttccgctc | 360 |
| actttcggcg gagggaccaa ggtggaaata aaacgaactg tggctgcacc atctgtcttc | 420 |
| atcttcccgc catctgatga gcagttgaaa tctggaactg cctctgttgt gtgcctgctg | 480 |
| aataacttct atcccagaga ggccaaagta cagtggaagg tggataacgc cctccaatcg | 540 |
| ggtaactccc aggagagtgt cacagagcag gacagcaagg acagcaccta cagcctcagc | 600 |
| agcaccctga cgctgagcaa agcagactac gagaaacaca agtctacgc ctgcgaagtc | 660 |
| acccatcagg gcctgagctc gcccgtcaca aagagcttca caggggaga gtgt | 714 |

<210> SEQ ID NO 18
<211> LENGTH: 1416
<212> TYPE: DNA
<213> ORGANISM: humanized antibody

<400> SEQUENCE: 18

| | |
|---|---|
| atggacaggc ttacttcctc attcctgctg ctgattgtcc ctgcatatgt cctgtcccag | 60 |
| gttactctga aagagtctgg ccctgtacta gtgaagccca ccgagaccct cactctgact | 120 |
| tgtactttct ctgggttttc actgagcact tctggtatgg gagtgagctg gattcgtcag | 180 |
| cctccaggaa aggctctgga gtggctggca cacatttact gggatgatga caagcgctat | 240 |
| aacccatccc tgaagagccg gctcacaatc tccaaggata cctccaaaag ccaggtagtc | 300 |
| ctcacgatga ccaatatgga ccctgtagat actgccacat actactgtgt cgaaggccc | 360 |
| attactccgg tactagtcga tgctatggac tactggggcc aaggaaccct ggtcaccgtc | 420 |
| tcctcagcct ccaccaaggg cccatcggtc ttccccctgg cacctcctc aagagcacc | 480 |
| tctgggggca gcgcggccct gggctgcctg gtcaaggact acttccccga accggtgacg | 540 |
| gtgtcgtgga actcaggcgc cctgaccagc ggcgtgcaca ccttcccggc tgtcctacag | 600 |
| tcctcaggac tctactccct cagcagcgtg gtgaccgtgc cctccagcag cttgggcacc | 660 |
| cagacctaca tctgcaacgt gaatcacaag cccagcaaca ccaaggtgga caagaaagtt | 720 |
| gagcccaaat cttgtgacaa aactcacaca tgcccaccgt gcccagcacc tgaactcctg | 780 |
| gggggaccgt cagtcttcct cttccccca aaacccaagg acaccctcat gatctcccgg | 840 |
| acccctgagg tcacatgcgt ggtggtggac gtgagccacg aagaccctga ggtcaagttc | 900 |
| aactggtacg tggacggcgt ggaggtgcat aatgccaaga caaagccgcg ggaggagcag | 960 |
| tacaacagca cgtaccgtgt ggtcagcgtc ctcaccgtcc tgcaccagga ctggctgaat | 1020 |
| ggcaaggagt acaagtgcaa ggtctccaac aaagccctcc cagcccccat cgagaaaacc | 1080 |
| atctccaaag ccaaagggca gccccgagaa ccacaggtgt acaccctgcc cccatcccgg | 1140 |
| gatgagctga ccaagaacca ggtcagcctg acctgcctgg tcaaaggctt ctatcccagc | 1200 |
| gacatcgccg tggagtggga gagcaatggg cagccggaga caactacaa gaccacgcct | 1260 |

```
cccgtgctgg actccgacgg ctccttcttc ctctacagca agctcaccgt ggacaagagc    1320
aggtggcagc aggggaacgt cttctcatgc tccgtgatgc atgaggctct gcacaaccac    1380
tacacgcaga gagcctctc cctgtctccg ggtaaa                               1416
```

```
<210> SEQ ID NO 19
<211> LENGTH: 238
<212> TYPE: PRT
<213> ORGANISM: humanized antibody

<400> SEQUENCE: 19

Met Lys Leu Pro Val Arg Leu Leu Val Leu Met Phe Trp Ile Pro Ala
1               5                   10                  15

Ser Ser Ser Asp Val Val Met Thr Gln Ser Pro Leu Ser Leu Pro Val
            20                  25                  30

Thr Leu Gly Gln Pro Ala Ser Ile Ser Cys Arg Ser Ser Gln Asn Ile
        35                  40                  45

Ile His Ser Asn Gly Asn Thr Tyr Leu Glu Trp Tyr Leu Gln Lys Pro
    50                  55                  60

Gly Gln Ser Pro Arg Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Phe Gln Gly Ser His Val Pro Leu Thr Phe Gly Gly Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 20
<211> LENGTH: 472
<212> TYPE: PRT
<213> ORGANISM: humanized antibody

<400> SEQUENCE: 20

Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Val Leu Val Lys
            20                  25                  30

Pro Thr Glu Thr Leu Thr Leu Thr Cys Thr Phe Ser Gly Phe Ser Leu
        35                  40                  45

Ser Thr Ser Gly Met Gly Val Ser Trp Ile Arg Gln Pro Pro Gly Lys
    50                  55                  60
```

```
Ala Leu Glu Trp Leu Ala His Ile Tyr Trp Asp Asp Lys Arg Tyr
 65                  70                  75                  80

Asn Pro Ser Leu Lys Ser Arg Leu Thr Ile Ser Lys Asp Thr Ser Lys
                 85                  90                  95

Ser Gln Val Val Leu Thr Met Thr Asn Met Asp Pro Val Asp Thr Ala
            100                 105                 110

Thr Tyr Tyr Cys Val Arg Arg Pro Ile Thr Pro Val Leu Val Asp Ala
        115                 120                 125

Met Asp Tyr Trp Gly Gln Gly Thr Leu Val Thr Val Ser Ser Ala Ser
130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Leu Gly Thr Gln Thr Tyr Ile
210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
450                 455                 460

Ser Leu Ser Leu Ser Pro Gly Lys
465                 470
```

HUMANIZED ANTIBODIES

This application claims priority of International Application No. US02/11854, filed Apr. 26, 2002, which claims the priority of United States provisional application No. 60/287,653, filed Apr. 30, 2001. The contents of each of these applications is incorporated herein by reference.

The invention relates to humanized antibodies useful for treating and preventing human diseases associated with amyloid β (Aβ), such as Alzheimer's disease, Down's syndrome, and cerebral amnyloid angiopathy. Mouse monoclonal antibody 10D5 was raised by immunizing mice with human Aβ1-28, and has been widely used in analytical methods [*J. Neuropathol. Exper. Neurology* 51:76-83 (1992); *Nature* 359:325-327 (1992); *Neuroscience Lett.* 172: 122-124 (1994); *Biochem. Biophys. Res. Commun.* 200: 1598-1603 (1994); *J. Neuropathol. Exper. Neurology* 53:377-383 (1994); *Annals Neurology* 37:512-518 (1995); *Annals Neurology* 41:809-813 (1997); *J. Neuroimmnunol.* 88:85-90 (1998); *J. Neuroimmnunol.* 95:136-142 (1999)]. 10D5 has been shown to bind to the N-terminal region of Aβ and has affinity of approximately 43 pM for aggregated Aβ.

After 10D5 was administered to a group of 8.5 to 10.5 month-old heterozygous, transgenic PDAPP mice ($APP^{V717F}$) at a weekly intraperitoneal dose of about 10 mg/kg for six months, the mice had significantly reduced levels of Aβ1-42 in brain cortex. However, the 10D5 group did not have a significant reduction of total Aβ in any tissue, nor of Aβ1-42 in hippocampus or cerebellum [Bard, F., et al., *Nature Med.* 6:916-919 (2000); WO 00/72876 and WO 00/72880, 7 Dec., 2000]. It was asserted that amyloid plaques in the 10D5 group also reduced in number and appearance, with some evidence of cell-associated immunoreactivity.

Another study in WO 00/72876 and WO 00/72880 reported that administration of 10D5 to older mice for six months caused a significant reduction in amyloid β plaque burden. It was asserted that the antibody gained access to the central nervous system in sufficient amounts to "decorate" β-amyloid plaques. Finally, it was stated that mouse 10D5 induces phagocytosis of amyloid plaques in in vitro studies.

Methods for administering aggregated Aβ1-42 to provoke an immunologic response and reduced amyloid deposits are described in PCT publication WO99/27944, published 10 Jun. 1999. The description postulates that full-length aggregated Aβ peptide would be a useful immunogen. The application also indicates that antibodies that bind to Aβ peptide could be used as alternate therapeutic agents. However, this appears to be speculation since the supporting data reflect protocols that involve active immunization using, for example, Aβ1-42.

WO 99/60024, published 25 Nov. 1999, is directed to methods for amyloid removal using anti-amyloid antibodies. The mechanism, however, is stated to utilize the ability of anti-Aβ antibodies to bind to pre-formed amyloid deposits (i.e. plaques) and result in subsequent microglial clearance of localized plaques. This mechanism was not proved in vivo. This publication further states that to be effective against Aβ plaques, anti-Aβ antibodies must be delivered directly to the brain, because antibodies cannot cross the blood brain barrier.

Queen, et al. describe methods of humanizing antibodies [e.g., U.S. Pat. Nos. 5,585,089, 5,693,761, 5,693,762, 6,180,370].

Humanized forms of 10D5 are needed for use in humans having Down's syndrome, or pre-clinical or clinical Alzheimer's disease or cerebral amyloid angiopathy (CAA). However, it is not known whether 10D5 can be humanized so that the humanized antibody retained the binding properties of the mouse antibody.

SUMMARY OF THE INVENTION

This invention provides humanized forms of 10D5. These humanized antibodies have binding properties (affinity and epitope location) that are approximately the same as those of the mouse 10D5 antibody. The invention includes antibodies, single chain antibodies, and fragments thereof. The invention includes antibodies wherein the CDR are those of mouse monoclonal antibody 10D5 (sequences SEQ ID NO:1 through SEQ ID NO:6) and wherein the antibodies retain approximately the binding properties of the mouse antibody and have in vitro and in vivo properties functionally equivalent to the mouse antibody. In another aspect, this invention provides humanized antibodies and fragments thereof, wherein the variable regions have sequences comprising the CDR from mouse antibody 10D5 and specific human framework sequences (sequences SEQ ID NO:7-SEQ ID NO:10), wherein the antibodies retain approximately the binding properties of the mouse antibody and have in vitro and in vivo properties functionally equivalent to the mouse antibody 10D5. In another aspect, this invention provides humanized antibodies and fragments thereof, wherein the light chain is SEQ ID NO:11 and the heavy chain is SEQ ID NO:12.

Also part of the invention are polynucleotide sequences that encode the humanized antibodies or fragments thereof disclosed above, vectors comprising the polynucleotide sequences encoding the humanized antibodies or fragments thereof, host cells transformed with the vectors or incorporating the polynucleotides that express the humanized antibodies or fragments thereof, pharmaceutical formulations of the humanized antibodies and fragments thereof disclosed herein, and methods of making and using the same.

Such humanized antibodies and fragments thereof are useful for, among other things, treating and preventing diseases and conditions characterized by Aβ plaques or Aβ toxicity in the brain, such as Alzheimer's disease, Down's syndrome, and cerebral amyloid angiopathy in humans.

The invention also includes use of a humanized antibody of the present invention for the manufacture of a medicament, including prolonged expression of recombinant sequences of the antibody or antibody fragment in human tissues, for treating, preventing, or reversing Alzheimer's disease, Down's syndrome, or cerebral amyloid angiopathy, or to inhibit the formation of amyloid plaques or the effects of toxic soluble Aβ species in humans.

DETAILED DESCRIPTION OF THE INVENTION

We have surprisingly found that humanized antibodies, wherein the CDRs originate from mouse monoclonal antibody 10D5 and the framework and other portions of the antibodies originate from a human germ line, bind Aβ1-40 and Aβ1-42 with at least the affinity with which mouse 10D5 binds Aβ. Thus, we have a reasonable basis for believing that humanized antibodies of this specificity, modified to reduce their immunogenicity by converting them to a humanized form, offer the opportunity to treat, both prophylactically and therapeutically, conditions in humans that are associated with formation of beta-amyloid plaques. These conditions include, as noted above, pre-clinical and clinical Alzheimer's, Down's syndrome, and pre-clinical and clinical cerebral amyloid angiopathy.

As used herein, the word "treat" includes therapeutic treatment, where a condition to be treated is already known to be present and prophylaxis—i.e., prevention of, or amelioration of, the possible future onset of a condition.

By "antibody" is meant a monoclonal antibody per se, or an immunologically effective fragment thereof, such as an Fab, Fab', or F(ab')$_2$ fragment thereof. In some contexts, herein, fragments will be mentioned specifically for emphasis; nevertheless, it will be understood that regardless of whether fragments are specified, the term "antibody" includes such fragments as well as single-chain forms. As long as the protein retains the ability specifically to bind its intended target, it is included within the term "antibody." Also included within the definition "antibody" are single chain forms. Preferably, but not necessarily, the antibodies useful in the invention are produced recombinantly. Antibodies may or may not be glycosylated, though glycosylated antibodies are preferred. Antibodies are properly cross-linked via disulfide bonds, as is well known.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as kappa and lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 3 or more amino acids.

The variable regions of each light/heavy chain pair form the antibody binding site. Thus, an intact antibody has two binding sites. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with well known conventions [Kabat, et al., "Sequences of Proteins of Immunological Interest" National Institutes of Health, Bethesda, Md., 1987 and 1991; Chothia, et al., J. Mol. Biol. 196:901-917 (1987); Chothia, et al., Nature 342:878-883 (1989)].

By "humanized antibody" is meant an antibody that is composed partially or fully of amino acid sequences derived from a human antibody germline by altering the sequence of an antibody having non-human complementarity determining regions (CDR). A humanized immunoglobulin does not encompass a chimeric antibody, having a mouse variable region and a human constant region. However, the variable region of the antibody and even the CDR are humanized by techniques that are by now well known in the art. The framework regions of the variable regions are substituted by the corresponding human framework regions leaving the non-human CDR substantially intact. As mentioned above, it is sufficient for use in the methods of the invention, to employ an immunologically specific fragment of the antibody, including fragments representing single chain forms.

Humanized antibodies have at least three potential advantages over non-human and chimeric antibodies for use in human therapy:

1) because the effector portion is human, it may interact better with the other parts of the human immune system (e.g., destroy the target cells more efficiently by complement-dependent cytotoxicity (CDC) or antibody-dependent cellular cytotoxicity (ADCC).

2) The human immune system should not recognize the framework or C region of the humanized antibody as foreign, and therefore the antibody response against such an injected antibody should be less than against a totally foreign non-human antibody or a partially foreign chimeric antibody.

3) Injected non-human antibodies have been reported to have a half-life in the human circulation much shorter than the half-life of human antibodies. Injected humanized antibodies will have a half-life essentially identical to naturally occurring human antibodies, allowing smaller and less frequent doses to be given.

The design of humanized immunoglobulins may be carried out as follows. As to the human framework region, a framework or variable region amino acid sequence of a CDR-providing non-human immunoglobulin is compared with corresponding sequences in a human immunoglobulin variable region sequence collection, and a sequence having a high percentage of identical amino acids is selected. When an amino acid falls under the following category, the framework amino acid of a human immunoglobulin to be used (acceptor immunoglobulin) is replaced by a framework amino acid from a CDR-providing non-human immunoglobulin (donor immunoglobulin):

(a) the amino acid in the human framework region of the acceptor immunoglobulin is unusual for human immunoglobulin at that position, whereas the corresponding amino acid in the donor immunoglobulin is typical for human immunoglobulin at that position;

(b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model [Queen, et al., Proc. Natl. Acad. Sci. USA 86:10029-10033 (1989), and Co, et al., Proc. Natl. Acad. Sci. USA 88, 2869 (1991)]. When each of the amino acid in the human framework region of the acceptor immunoglobulin and a corresponding amino acid in the donor immunoglobulin is unusual for human immunoglobulin at that position, such an amino acid is replaced by an amino acid typical for human immunoglobulin at that position.

A preferred humanized antibody is a humanized form of mouse antibody 10D5. The CDRs of humanized 10D5 have the following amino acid sequences:

```
light chain CDR1:
1               5              10              15
```

-continued

```
Arg Ser Ser Gln Asn Ile Ile His Ser Asn Gly Asn Thr Tyr Leu Glu   (SEQ ID NO: 1)

light chain CDR2:
  1               5
Lys Val Ser Asn Arg Phe Ser                                        (SEQ ID NO: 2)

light chain CDR3:
  1               5
Phe Gln Gly Ser His Val Pro Leu Thr                                (SEQ ID NO: 3)

heavy chain CDR1:
  1               5
Thr Ser Gly Met Gly Val Ser                                        (SEQ ID NO: 4)

heavy chain CDR2:
  1               5                    10                   15
His Ile Tyr Trp Asp Asp Lys Arg Tyr Asn Pro Ser Leu Lys Ser        (SEQ ID NO: 5)

and, heavy chain CDR3:
  1               5                    10
Arg Pro Ile Thr Pro Val Leu Val Asp Ala Met Asp Tyr.               (SEQ ID NO: 6)
```

A preferred light chain variable region of a humanized antibody of the present invention has the following amino acid sequence, in which the framework originated from human germline Vk segment DPK18 and J segment Jk4:

```
  1                    5                          10                         15
Asp Val Xaa Met Thr Gln Xaa Pro Leu Ser Leu Pro Val Xaa Leu Gly   (SEQ ID NO: 7)

20                         25                          30
Xaa Pro Ala Ser Ile Ser Cys Arg Ser Ser Gln Asn Ile Xaa His Ser 35                         40                         45
Asn Gly Asn Thr Tyr Leu Glu Trp Tyr Leu Gln Lys Pro Gly Gln Ser 50                         55                         60
Pro Xaa Leu Leu Ile Tyr Lys Val Ser Asn Arg Phe Ser Gly Val Pro 65                         70                         75                         80
Asp Arg Phe Ser Gly Ser Gly Ser Gly Thr Asp Phe Thr Leu Lys Ile 85                         90                         95
Ser Arg Val Glu Ala Glu Asp Xaa Gly Val Tyr Tyr Cys Phe Gln Gly 100                        105                        110
Ser His Val Pro Leu Thr Phe Gly Xaa Gly Thr Lys Xaa Glu Ile Lys

Arg.
``` wherein:
   Xaa at position 3 is Val or Leu;
   Xaa at position 7 is Ser or Thr;
   Xaa at position 14 is Thr or Ser;
   Xaa at position 17 is Gln, Asp, or Asn;
   Xaa at position 30 is Ile or Val;
   Xaa at position 50 is Arg or Lys;
   Xaa at position 88 is Val or Leu;
   Xaa at position 105 is Gly or Ala; and
   Xaa at position 109 is Val or Leu.

A preferred heavy chain variable region of a humanized antibody of the present invention has the following amino acid sequence, in which the framework originated from human germline VH segment DP-28 and J segment JH4, with several amino acid substitutions to the consensus amino acids in the same human subgroup to reduce potential immunogenicity:

```
  1                    5                          10                         15
Xaa Xaa Thr Leu Lys Glu Ser Gly Pro Val Leu Val Lys Pro Thr Glu   (SEQ ID NO: 8)

20                         25                         30
Thr Leu Thr Leu Thr Cys Thr Phe Ser Gly Phe Ser Leu Ser Thr Ser 35                         40                         45
Gly Met Gly Val Ser Trp Ile Arg Gln Pro Pro Gly Lys Ala Leu Glu 50                         55                         60
Trp Leu Ala His Ile Tyr Trp Asp Asp Lys Arg Tyr Asn Pro Xaa 65                         70                         75                         80
```

```
                                  -continued
Leu Lys Ser Ary Leu Thr Ile Ser Lys Asp Thr Ser Xaa Xaa Gln Val 85                  90                  95
Val Leu Xaa Xaa Thr Xaa Xaa Asp Pro Val Asp Thr Ala Thr Tyr Tyr 100                 105                 110
Cys Val Arg Arg Pro Ile Thr Pro Val Leu Val Asp Ala Met Asp Tyr 115                 120
Trp Gly Gln Gly Thr Xaa Val Thr Val Ser Ser.
``` wherein:
  Xaa at position 1 is Gln or Glu;
  Xaa at position 2 is Val or Ala;
  Xaa at position 64 is Ser or Thr;
  Xaa at position 77 is Lys or Arg;
  Xaa at position 78 is Ser or Thr;
  Xaa at position 83 is Thr or Ser;
  Xaa at position 84 is Met, Ile, or Leu;
  Xaa at position 86 is Asn, Ser, or Thr;
  Xaa at position 87 is Met, Val, or Leu; and
  Xaa at position 118 is Leu or Ser.

A particularly preferred light chain variable region of a humanized antibody of the present invention has the following amino acid sequence, in which the framework originated from human germline Vk segment DPK18 and J segment Jk4:

```
1               5                   10                  15
Asp Val Val Met Thr Gln Ser Pro Leu Ser Leu Pro Val Thr Leu Gly   (SEQ ID NO: 9)

20                  25                  30
Gln Pro Ala Ser Ile Ser Cys Arg Ser Ser Gln Asn Ile Ile His Ser 35                  40                  45
Asn Gly Asn Thr Tyr Leu Glu Trp Tyr Leu Gln Lys Pro Gly Gln Ser 50                  55                  60
Pro Arg Leu Leu Ile Tyr Lys Val Ser Asn Arg Phe Ser Gly Val Pro 65                  70                  75                  80
Asp Arg Phe Ser Gly Ser Gly Ser Gly Thr Asp Phe Thr Leu Lys Ile 85                  90                  95
Ser Arg Val Glu Ala Glu Asp Val Gly Val Tyr Tyr Cys Phe Gln Gly 100                 105                 110
Ser His Val Pro Leu Thr Phe Gly Gly Gly Thr Lys Val Glu Ile Lys

Arg.
```

A particularly preferred heavy chain variable region of a humanized antibody of the present invention has the following amino acid sequence, in which the framework originated from human germline VH segment DP-28 and J segment JH4:

```
1               5                   10                  15
Gln Val Thr Leu Lys Glu Ser Gly Pro Val Leu Val Lys Pro Thr Glu   (SEQ ID NO: 10)

20                  25                  30
Thr Leu Thr Leu Thr Cys Thr Phe Ser Gly Phe Ser Leu Ser Thr Ser 35                  40                  45
Gly Met Gly Val Ser Trp Ile Arg Gln Pro Pro Gly Lys Ala Leu Glu 50                  55                  60
Trp Leu Ala His Ile Tyr Trp Asp Asp Asp Lys Arg Tyr Asn Pro Ser
```

-continued

```
 65                  70                  75                  80
Leu Lys Ser Arg Leu Thr Ile Ser Lys Asp Thr Ser Lys Ser Gln Val 85                  90                  95
Val Leu Thr Met Thr Asn Met Asp Pro Val Asp Thr Ala Thr Tyr Tyr 100                 105                 110
Cys Val Arg Arg Pro Ile Thr Pro Val Leu Val Asp Ala Met Asp Tyr 115                 120
Trp Gly Gln Gly Thr Leu Val Thr Val Ser Ser.
```

A preferred light chain for a humanized antibody of the present invention has the amino acid sequence:

```
  1                   5                  10                  15
Asp Val Val Met Thr Gln Ser Pro Leu Ser Leu Pro Val Thr Leu Gly   (SEQ ID NO: 11)

20                  25                  30
Gln Pro Ala Ser Ile Ser Cys Arg Ser Ser Gln Asn Ile Ile His Ser 35                  40                  45
Asn Gly Asn Thr Tyr Leu Glu Trp Tyr Leu Gln Lys Pro Gly Gln Ser 50                  55                  60
Pro Arg Leu Leu Ile Tyr Lys Val Ser Asn Arg Phe Ser Gly Val Pro 65                  70                  75                  80
Asp Arg Phe Ser Gly Ser Gly Ser Gly Thr Asp Phe Thr Leu Lys Ile 85                  90                  95
Ser Arg Val Glu Ala Glu Asp Val Gly Val Tyr Tyr Cys Phe Gln Gly 100                 105                 110
Ser His Val Pro Leu Thr Phe Gly Gly Gly Thr Lys Val Glu Ile Lys 115                 120                 125
Arg Thr Val Ala Ala Pro Ser Val Phe Ile Phe Pro Pro Ser Asp Glu 130                 135                 140
Gln Leu Lys Ser Gly Thr Ala Ser Val Val Cys Leu Leu Asn Asn Phe 145                 150                 155                 160
Tyr Pro Arg Glu Ala Lys Val Gln Trp Lys Val Asp Asn Ala Leu Gln 165                 170                 175
Ser Gly Asn Ser Gln Glu Ser Val Thr Glu Gln Asp Ser Lys Asp Ser 180                 185                 190
Thr Tyr Ser Leu Ser Ser Thr Leu Thr Leu Ser Lys Ala Asp Tyr Glu 195                 200                 205
Lys His Lys Val Tyr Ala Cys Glu Val Thr His Gln Gly Leu Ser Ser 210                 215
Pro Val Thr Lys Ser Phe Asn Arg Gly Glu Cys.
```

A preferred heavy chain for a humanized antibody of the present invention has the amino acid sequence:

```
  1                   5                  10                  15
Gln Val Thr Leu Lys Glu Ser Gly Pro Val Leu Val Lys Pro Thr Glu   (SEQ ID NO: 12)

20                  25                  30
Thr Leu Thr Leu Thr Cys Thr Phe Ser Gly Phe Ser Leu Ser Thr Ser 35                  40                  45
Gly Met Gly Val Ser Trp Ile Arg Gln Pro Pro Gly Lys Ala Leu Glu 50                  55                  60
Trp Leu Ala His Ile Tyr Trp Asp Asp Asp Lys Arg Tyr Asn Pro Ser
```

-continued

```
             65                      70                      75                      80
Leu Lys Ser Arg Leu Thr Ile Ser Lys Asp Thr Ser Lys Ser Gln Val 85                      90                      95
Val Leu Thr Met Thr Asn Met Asp Pro Val Asp Thr Ala Thr Tyr Tyr 100                     105                     110
Cys Val Arg Arg Pro Ile Thr Pro Val Leu Val Asp Ala Met Asp Tyr 115                     120                     125
Trp Gly Gln Gly Thr Leu Val Thr Val Ser Ser Ala Ser Thr Lys Gly 130                     135                     140
Pro Ser Val Phe Pro Leu Ala Pro Ser Ser Lys Ser Thr Ser Gly Gly 145                     150                     155                     160
Thr Ala Ala Leu Gly Cys Leu Val Lys Asp Tyr Phe Pro Glu Pro Val 165                     170                     175
Thr Val Ser Trp Asn Ser Gly Ala Leu Thr Ser Gly Val His Thr Phe 180                     185                     190
Pro Ala Val Leu Gln Ser Ser Gly Leu Tyr Ser Leu Ser Ser Val Val 195                     200                     205
Thr Val Pro Ser Ser Ser Leu Gly Thr Gln Thr Tyr Ile Cys Asn Val 210                     215                     220
Asn His Lys Pro Ser Asn Thr Lys Val Asp Lys Lys Val Glu Pro Lys 225                     230                     235                     240
Ser Cys Asp Lys Thr His Thr Cys Pro Pro Cys Pro Ala Pro Glu Leu 245                     250                     255
Leu Gly Gly Pro Ser Val Phe Leu Phe Pro Pro Lys Pro Lys Asp Thr 260                     265                     270
Leu Met Ile Ser Arg Thr Pro Glu Val Thr Cys Val Val Val Asp Val 275                     280                     285
Ser His Glu Asp Pro Glu Val Lys Phe Asn Trp Tyr Val Asp Gly Val 290                     295                     300
Glu Val His Asn Ala Lys Thr Lys Pro Arg Glu Glu Gln Tyr Asn Ser 305                     310                     315                     320
Thr Tyr Arg Val Val Ser Val Leu Thr Val Leu His Gln Asp Trp Leu 325                     330                     335
Asn Gly Lys Glu Tyr Lys Cys Lys Val Ser Asn Lys Ala Leu Pro Ala 340                     345                     350
Pro Ile Glu Lys Thr Ile Ser Lys Ala Lys Gly Gln Pro Arg Glu Pro 355                     360                     365
Gln Val Tyr Thr Leu Pro Pro Ser Arg Asp Glu Leu Thr Lys Asn Gln 370                     375                     380
Val Ser Leu Thr Cys Leu Val Lys Gly Phe Tyr Pro Ser Asp Ile Ala 385                     390                     395                     400
Val Glu Trp Glu Ser Asn Gly Gln Pro Glu Asn Asn Tyr Lys Thr Thr 405                     410                     415
Pro Pro Val Leu Asp Ser Asp Gly Ser Phe Phe Leu Tyr Ser Lys Leu 420                     425                     430
Thr Val Asp Lys Ser Arg Trp Gln Gln Gly Asn Val Phe Ser Cys Ser 435                     440                     445
Val Met His Glu Ala Leu His Asn His Tyr Thr Gln Lys Ser Leu Ser

450
Leu Ser Pro Gly Lys.
```

Other sequences are possible for the light and heavy chains for humanized 10D5. The immunoglobulins can have two pairs of light chain/heavy chain complexes, at least one chain comprising one or more mouse complementarity determining regions functionally joined to human framework region segments.

In another aspect, the present invention is directed to recombinant polynucleotides encoding antibodies which, when expressed, comprise the heavy and light chain CDRs from an antibody of the present invention. Exemplary polynucleotides, which on expression code for the polypeptide chains comprising the heavy and light chain CDRs of monoclonal antibody 10D5 are given herein. Due to codon degeneracy, other polynucleotide sequences can be readily substituted for those sequences. Particularly preferred polynucleotides of the present invention encode antibodies, which when expressed, comprise the CDRs of SEQ ID NO:1-SEQ ID NO:6, or any of the variable regions of SEQ ID NO:7-SEQ ID NO:10, or the light and heavy chains of SEQ ID NO:11 and SEQ ID NO:12.

The polynucleotides will typically further include an expression control polynucleotide sequence operably linked to the humanized imnuunoglobulin coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host cell line, the host cell is propagated under conditions suitable for expressing the nucleotide sequences, and, as desired, the collection and purification of the light chains, heavy chains, light/heavy chain dimers or intact antibodies, binding fragments or other immunoglobulin forms may follow.

The nucleic acid sequences of the present invention capable of ultimately expressing the desired humanized antibodies can be formed from a variety of different polynucleotides (genomic or cDNA, RNA, synthetic oligonucleotides, etc.) and components (e.g., V, J, D, and C regions), using any of a variety of well known techniques. Joining appropriate genomic and synthetic sequences is a common method of production, but cDNA sequences may also be utilized.

Below is a cDNA sequence (SEQ ID NO:17), from which the light chain having the amino acid sequence of SEQ ID NO:19 may be expressed.

```
         ATGAAGTTGCCTGTTAGGCTGTTGGTACTGATGTTCTGGATTCCTGCTTCCAGCAGTGAT      (SEQ ID NO: 17)

1---------+---------+---------+---------+---------+---------+   60

M   K   L   P   V   R   L   L   V   L   M   F   W   I   P   A   S   S   S   D    -  (SEQ ID NO: 19)

GTTGTGATGACCCAATCTCCACTCTCCCTGCCTGTCACTCTTGGACAGCCAGCCTCCATC

61---------+---------+---------+---------+---------+---------+  120

V   V   M   T   Q   S   P   L   S   L   P   V   T   L   G   Q   P   A   S   I    -

TCTTGCAGATCTAGTCAGAACATTATACATAGTAATGGAAACACCTATTTAGAATGGTAC

121---------+---------+---------+---------+---------+---------+  180

S   C   R   S   S   Q   N   I   I   H   S   N   G   N   T   Y   L   E   W   Y    -

CTGCAGAAACCAGGCCAGTCTCCAAGGCTCCTGATCTACAAAGTTTCCAACCGATTTTCT

181---------+---------+---------+---------+---------+---------+  240

L   Q   K   P   G   Q   S   P   R   L   L   I   Y   K   V   S   N   R   F   S    -

GGGGTCCCAGACAGGTTCAGTGGCAGTGGATCAGGGACAGATTTCACACTCAAGATCAGC

241---------+---------+---------+---------+---------+---------+  300

G   V   P   D   R   F   S   G   S   G   S   G   T   D   F   T   L   K   I   S    -

AGAGTGGAGGCTGAGGATGTGGGAGTTTATTACTGCTTTCAAGGTTCACATGTTCCGCTC

301---------+---------+---------+---------+---------+---------+  360

R   V   E   A   E   D   V   G   V   Y   Y   C   F   Q   G   S   H   V   P   L    -

ACTTTCGGCGGAGGGACCAAGGTGGAAATAAAACGAACTGTGGCTGCACCATCTGTCTTC

361---------+---------+---------+---------+---------+---------+  420

T   F   G   G   G   T   K   V   E   I   K   R   T   V   A   A   P   S   V   F    -

ATCTTCCCGCCATCTGATGAGCAGTTGAAATCTGGAACTGCCTCTGTTGTGTGCCTGCTG

421---------+---------+---------+---------+---------+---------+  480

I   F   P   P   S   D   E   Q   L   K   S   G   T   A   S   V   V   C   L   L    -

AATAACTTCTATCCCAGAGAGGCCAAAGTACAGTGGAAGGTGGATAACGCCCTCCAATCG

481---------+---------+---------+---------+---------+---------+  540

N   N   F   Y   P   R   E   A   K   V   Q   W   K   V   D   N   A   L   Q   S    -
```

-continued

```
      GGTAACTCCCAGGAGAGTGTCACAGAGCAGGACAGCAAGGACAGCACCTACAGCCTCAGC
541 ---------+---------+---------+---------+---------+---------+   600
    G  N  S  Q  E  S  V  T  E  Q  D  S  K  D  S  T  Y  S  L  S    —

AGCACCCTGACGCTGAGCAAAGCAGACTACGAGAAACACAAAGTCTACGCCTGCGAAGTC
601 ---------+---------+---------+---------+---------+---------+   660
    S  T  L  T  L  S  K  A  D  Y  E  K  H  K  V  Y  A  C  E  V    —

ACCCATCAGGGCCTGAGCTCGCCCGTCACAAAGAGCTTCAACAGGGGAGAGTGT
661 ---------+---------+---------+---------+---------+----         714
    T  H  Q  G  L  S  S  P  V  T  K  S  P  N  R  G  E  C          —
```

Below is a cDNA sequence (SEQ ID NO:18), from which the heavy chain having the amino acid sequence of SEQ ID NO:20 may be expressed.

```
      ATGGACAGGCTTACTTCCTCATTCCTGCTGCTGATTGTCCCTGCATATGTCCTGTCCCAG       (SEQ ID NO: 18)
  1 ---------+---------+---------+---------+---------+---------+   60
    M  D  R  L  T  S  S  F  L  L  L  I  V  P  A  Y  V  L  S  Q    —  (SEQ ID NO: 20)

GTTACTCTGAAAGAGTCTGGCCCTGTACTAGTGAAGCCCACCGAGACCCTCACTCTGACT
 61 ---------+---------+---------+---------+---------+---------+   120
    V  T  L  K  E  S  G  P  V  L  V  K  P  T  E  T  L  T  L  T    —

TGTACTTTCTCTGGGTTTTCACTGAGCACTTCTGGTATGGGAGTGAGCTGGATTCGTCAG
121 ---------+---------+---------+---------+---------+---------+   180
    C  T  F  S  G  F  S  L  S  T  S  G  M  G  V  S  W  I  R  Q    —

CCTCCAGGAAAGGCTCTGGAGTGGCTGGCACACATTTACTGGGATGATGACAAGCGCTAT
181 ---------+---------+---------+---------+---------+---------+   240
    P  P  G  K  A  L  E  W  L  A  H  I  Y  W  D  D  D  K  R  Y    —

AACCCATCCCTGAAGAGCCGGCTCACAATCTCCAAGGATACCTCCAAAAGCCAGGTAGTC
241 ---------+---------+---------+---------+---------+---------+   300
    N  P  S  L  K  S  R  L  T  I  S  K  D  T  S  K  S  Q  V  V    —

CTCACGATGACCAATATGGACCCTGTAGATACTGCCACATACTACTGTGTTCGAAGGCCC
301 ---------+---------+---------+---------+---------+---------+   360
    L  T  M  T  N  M  D  P  V  D  T  A  T  Y  Y  C  V  R  R  P    —

ATTACTCCGGTACTAGTCGATGCTATGGACTACTGGGGCCAAGGAACCCTGGTCACCGTC
361 ---------+---------+---------+---------+---------+---------+   420
    I  T  P  V  L  V  D  A  M  D  Y  W  G  Q  G  T  L  V  T  V    —

TCCTCAGCCTCCACCAAGGGCCCATCGGTCTTCCCCCTGGCACCCTCCTCCAAGAGCACC
421 ---------+---------+---------+---------+---------+---------+   480
    S  S  A  S  T  K  G  P  S  V  F  P  L  A  P  S  S  K  S  T    —

TCTGGGGGCACAGCGGCCCTGGGCTGCCTGGTCAAGGACTACTTCCCCGAACCGGTGACG
481 ---------+---------+---------+---------+---------+---------+   540
    S  G  G  T  A  A  L  G  C  L  V  K  D  Y  F  P  E  P  V  T    —
```

-continued

```
       GTGTCGTGGAACTCAGGCGCCCTGACCAGCGGCGTGCACACCTTCCCGGCTGTCCTACAG
541    ---------+---------+---------+---------+---------+---------+    600
         V  S  W  N  S  G  A  L  T  S  G  V  H  T  F  P  A  V  L  Q  -

TCCTCAGGACTCTACTCCCTCAGCAGCGTGGTGACCGTGCCCTCCAGCAGCTTGGGCACC
601    ---------+---------+---------+---------+---------+---------+    660
         S  S  G  L  Y  S  L  S  S  V  V  T  V  P  S  S  S  L  G  T  -

CAGACCTACATCTGCAACGTGAATCACAAGCCCAGCAACACCAAGGTGGACAAGAAAGTT
661    ---------+---------+---------+---------+---------+---------+    720
         Q  T  Y  I  C  N  V  N  H  K  P  S  N  T  K  V  D  K  K  V  -

GAGCCCAAATCTTGTGACAAAACTCACACATGCCCACCGTGCCCAGCACCTGAACTCCTG
721    ---------+---------+---------+---------+---------+---------+    780
         E  P  K  S  C  D  K  T  H  T  C  P  P  C  P  A  P  E  L  L  -

GGGGGACCGTCAGTCTTCCTCTTCCCCCCAAAACCCAAGGACACCCTCATGATCTCCCGG
781    ---------+---------+---------+---------+---------+---------+    840
         G  G  P  S  V  F  L  F  P  P  K  P  K  D  T  L  M  I  S  R  -

ACCCCTGAGGTCACATGCGTGGTGGTGGACGTGAGCCACGAAGACCCTGAGGTCAAGTTC
841    ---------+---------+---------+---------+---------+---------+    900
         T  P  E  V  T  C  V  V  V  D  V  S  H  E  D  P  E  V  K  F  -

AACTGGTACGTGGACGGCGTGGAGGTGCATAATGCCAAGACAAAGCCGCGGGAGGAGCAG
901    ---------+---------+---------+---------+---------+---------+    960
         N  W  Y  V  D  G  V  E  V  H  N  A  K  T  K  P  R  E  E  Q  -

TACAACAGCACGTACCGTGTGGTCAGCGTCCTCACCGTCCTGCACCAGGACTGGCTGAAT
961    ---------+---------+---------+---------+---------+---------+   1020
         Y  N  S  T  Y  R  V  V  S  V  L  T  V  L  H  Q  D  W  L  N  -

GGCAAGGAGTACAAGTGCAAGGTCTCCAACAAAGCCCTCCCAGCCCCCATCGAGAAAACC
1021   ---------+---------+---------+---------+---------+---------+   1080
         G  K  E  Y  K  C  K  V  S  N  K  A  L  P  A  P  I  E  K  T  -

ATCTCCAAAGCCAAAGGGCAGCCCCGAGAACCACAGGTGTACACCCTGCCCCCATCCCGG
1081   ---------+---------+---------+---------+---------+---------+   1140
         I  S  K  A  K  G  Q  P  R  E  P  Q  V  Y  T  L  P  P  S  R  -

GATGAGCTGACCAAGAACCAGGTCAGCCTGACCTGCCTGGTCAAAGGCTTCTATCCCAGC
1141   ---------+---------+---------+---------+---------+---------+   1200
         D  E  L  T  K  N  Q  V  S  L  T  C  L  V  K  G  F  Y  P  S  -

GACATCGCCGTGGAGTGGGAGAGCAATGGGCAGCCGGAGAACAACTACAAGACCACGCCT
1201   ---------+---------+---------+---------+---------+---------+   1260
         D  I  A  V  E  W  E  S  N  G  Q  P  E  N  N  Y  K  T  T  P  -

CCCGTGCTGGACTCCGACGGCTCCTTCTTCCTCTACAGCAAGCTCACCGTGGACAAGAGC
1261   ---------+---------+---------+---------+---------+---------+   1320
         P  V  L  D  S  D  G  S  F  F  L  Y  S  K  L  T  V  D  K  S  -

AGGTGGCAGCAGGGGAACGTCTTCTCATGCTCCGTGATGCATGAGGCTCTGCACAACCAC
```

-continued

```
1321 ---------+---------+---------+---------+---------+ 1380
     R  W  Q  Q  G  N  V  F  S  C  S  V  M  H  E  A  L  H  N  H   —
     TACACGCAGAAGAGCCTCTCCCTGTCTCCGGGTAAA
1381 ---------+---------+---------+------             1416
     Y  T  Q  K  S  L  S  L  S  P  G  K                —
```

The complete sequence of a humanized 10D5 light chain gene with introns (located between MluI and BamHI sites, as in pVk-Hu10D5) is shown below (SEQ ID NO:15). The nucleotide number indicates its position in pVk-Hu10D5. The $V_k$ and $C_k$ exons are translated in single letter code; the dot indicates the translation termination codon. The mature light chain starts at the double-underlined aspartic acid (D). The intron sequences are in italic. The expressed light chain corresponds to SEQ ID NO:11 when mature.

```
 619 ACGCGTCCACCATGAAGTTGCCTGTTAGGCTGTTGGTACTGATGTTCTGGATTCCTGCTTCCAGCAGTGATGTTGTGATG    (SEQ ID NO: 15)
              M  K  L  P  V  R  L  L  V  L  M  F  W  I  P  A  S  S  S  D  V  V  M
 699 ACCCAATCTCCACTCTCCCTGCCTGTCACTCTTGGACAGCCAGCCTCCATCTCTTGCAGATCTAGTCAGAACATTATACA
      T  Q  S  P  L  S  L  P  V  T  L  G  Q  P  A  S  I  S  C  R  S  S  Q  N  I  I  H
 779 TAGTAATGGAAACACCTATTTAGAATGGTACCTGCAGAAACCAGGCCAGTCTCCAAGGCTCCTGATCTACAAAGTTTCCA
       S  N  G  N  T  Y  L  E  W  Y  L  Q  K  P  G  Q  S  P  R  L  L  I  Y  K  V  S
 859 ACCGATTTTCTGGGGTCCCAGACAGGTTCAGTGGCAGTGGATCAGGGACAGATTTCACACTCAAGATCAGCAGAGTGGAG
       N  R  F  S  Q  V  P  D  R  F  S  G  S  G  S  G  T  D  F  T  L  K  I  S  R  V  E
 939 GCTGAGGATGTGGGAGTTTATTACTGCTTTCAAGGTTCACATGTTCCGCTCACTTTCGGCGGAGGGACCAAGGTGGAAAT
       A  E  D  V  G  V  Y  Y  C  F  Q  G  S  H  V  P  L  T  F  G  G  G  T  K  V  E  I
1019 AAAACGTAAGTGCACTTTCCTAATCTAGAAATTCTAAACTCTGAGGGGGTCGCATGACGTGGCCATTCTTTGCCTAAAGC
       K  R
1099 ATTGAGTTTACTGCAAGGTCAGAAAAGCATGCAAAGCCCTCAGAATGGCTGCAAAGAGCTCCAACAAAACAATTTAGAAC
1179 TTTATTAAGGAATAGGGGGAAGCTAGGAAGAAACTCAAAACATCAAGATTTTAAATACGCTTCTTGGTCTCCTTGCTATA
1259 ATTATCTGGGATAAGCATGCTGTTTTCTGTCTGTCCCTAACATGCCCTGTGATTATCCGCAAACAACACACCCAAGGGCA
1339 GAACTTTGTTACTTAAACACCATCCTGTTTGCTTCTTTCCTCAGGAACTGTGGCTGCACCATCTGTCTTCATCTTCCCGC
                                                           T  V  A  A  P  S  V  F  I  F  P
1419 CATCTGATGAGCAGTTGAAATCTGGAACTGCCTCTGTTGTGTGCGTGCTGAATAACTTCTATCCCAGAGAGGCCAAAGTA
      P  S  D  E  Q  L  K  S  G  T  A  S  V  V  C  L  L  N  N  F  Y  P  R  E  A  K  V
1499 CAGTGGAAGGTGGATAACGCCCTCCAATCGGGTAACTCCCAGGAGAGTGTCACAGAGCAGGACAGCAAGGACAGCACCTA
       Q  W  K  V  D  N  A  L  Q  S  G  N  S  Q  E  S  V  T  E  Q  D  S  K  D  S  T  Y
1579 CAGCCTCAGCAGCACCCTGACGCTGAGCAAAGCAGACTACGAGAAACACAAAGTCTACGCCTGCGAAGTCACCCATCAGG
        S  L  S  S  T  L  T  L  S  K  A  D  Y  E  K  H  K  V  Y  A  C  E  V  T  H  Q
1659 GCCTGAGCTCGCCCGTCACAAAGAGCTTCAACAGGGGAGAGTGTTAGAGGGAGAAGTGCCCCCACCTGCTCCTCAGTTCC
       G  L  S  S  P  V  T  K  S  F  N  R  G  E  C  .
1739 AGCCTGACCCCCTCCCATCCTTTGGCCTCTGACCCTTTTTCCACAGGGGACCTACCCCTATTGCGGTCCTCCAGCTCATC
1819 TTTCACCTCACCCCCCTCCTCCTCCTTGGCTTTAATTATGCTAATGTTGGAGGAGAATGAATAAATAAA  GTGAATCTTTG
```

-continued
```
1899 CACCTGTGGTTTCTCTCTTTCCTCATTTAATAATTATTATCTGTTGTTTTACCAACTACTCAATTTCTCTTATAAGGGAC 1979 TAAATATGTAGTCATCCTAAGGCGCATAACCATTTATAAAAATCATCCTTCATTCTATTTTACCCTATCATCCTCTGCAA 2059 GACAGTCCTCCCTCAAACCCACAAGCCTTCTGTCCTCACAGTCCCCTGGGCCATGGTAGGAGAGACTTGCTTCCTTGTTT 2139 TCCCCTCCTCAGCAAGCCCTCATAGTCCTTTTTAAGGGTGACAGGTCTTACAGTCATATATCCTTTGATTCAATTCCCTG 2219 AGAATCAACCAAAGCAAATTTTTCAAAAGAAGAAACCTGCTATAAAGAGAATCATTCATTGCAACATGATATAAAATAAC 2299 AACACAATAAAAGCAATTAAATAAACAAACAATAGGGAAATGTTTAAGTTCATCATGGTACTTAGACTTAATGGAATGTC 2379 ATGCCTTATTTACATTTTTAAACAGGTACTGAGGGACTCCTGTCTGCCAAGGGCCGTATTGAGTACTTTCCACAACCTAA 2459 TTTAATCCACACTATACTGTGAGATTAAAAACATTCATTAAAATGTTGCAAAGGTTCTATAAAGCTGAGAGACAAATATA

2539 TTCTATAACTCAGCAATCCCACTTCTAGGATCC
```

The complete sequence of a humanized 10D5 heavy chain gene with introns (located between MluI and BamHI sites, as in pVg1-Hu10D5) is shown below (SEQ ID NO:16). The nucleotide number indicates its position in pVg1-Hu10D5. The $V_H$ and $C_H$ exons are translated in single letter code; the dot indicates the translation termination codon. The mature heavy chain starts at the double-underlined glutamine (Q). The intron sequences are in italic. The expressed heavy chain corresponds to SEQ ID NO:12 when mature.

```
 619 ACGCGTCCACCATGGACAGGCTTACTTCCTCATTCCTGCTGCTGATTGTCCCTGCATATGTCCTGTCCCAGGTTACTCTG    (SEQ ID NO: 16)
             M  D  R  L  T  S  S  F  L  L  L  I  V  P  A  Y  V  L  S  Q  V  T  L

699 AAAGAGTCTGGCCCTGTACTAGTGAAGCCCACCGAGACCCTCACTCTGACTTGTACTTTCTCTGGGTTTTCACTGAGCAC
        K  E  S  G  P  V  L  V  K  P  T  E  T  L  T  L  T  C  T  F  S  G  F  S  L  S  T

779 TTCTGGTATGGGAGTGAGCTGGATTCGTCAGCCTCCAGGAAAGGCTCTGGAGTGGCTGGCACACATTTACTGGGATGATG
        S  G  M  G  V  S  W  I  R  Q  P  P  G  K  A  L  E  W  L  A  H  I  Y  W  D  D

859 ACAAGCGCTATAACCCATCCCTGAAGAGCCGGCTCACAATCTCCAAGGATACCTCCAAAAGCCAGGTAGTCCTCACGATG
        D  K  R  Y  N  P  S  L  K  S  R  L  T  I  S  K  D  T  S  K  S  Q  V  V  L  T  M

939 ACCAATATGGACCCTGTAGATACTGCCACATACTACTGTGTTCGAAGGCCCATTACTCCGGTACTAGTCGATGCTATGGA
        T  N  M  D  P  V  D  T  A  T  Y  Y  C  V  R  R  P  I  T  P  V  L  V  D  A  M  D

1019 CTACTGGGGCCAAGGAACCCTGGTCACCGTCTCCTCAGGTGAGTCCTCACAACCTCTAGAGCTTTCTGGGGCAGGCCAGG
        Y  W  G  Q  G  T  L  V  T  V  S  S

1099 CCTCACCTTGGCTTTGGGGCACGGAGCGGGCTAAGCTGAGGCAGGTGGCGCCAGCCAGGTGCACACCCAATGCCCATGAG

1179 CCCAGACACTGGACGCTGAACCTCGCGGACAGTTAAGAACCCAGGGGCCTCTGCGCCCTGGGCCCAGCTCTGTCCCACAC

1259 CGCGGTCACATGGCACCACCTCTCTTGCAGCCTCCACCAAGGGCCCATCGGTCTTCCCCCTGGCACCCTCCTCCAAGAGC
                                                A  S  T  K  G  P  S  V  F  P  L  A  P  S  S  K  S

1339 ACCTCTGGGGGCACAGCGGCCCTGGGCTGCCTGGTCAAGGACTACTTCCCCGAACCGGTGACGGTGTCGTGGAACTCAGG
        T  S  G  G  T  A  A  L  G  C  L  V  K  D  Y  F  P  E  P  V  T  V  S  W  N  S  G

1419 CGCCCTGACCAGCGGCGTGCACACCTTCCCGGCTGTCCTACAGTCCTCAGGACTCTACTCCCTCAGCAGCGTGGTGACCG
        A  L  T  S  G  V  H  T  F  P  A  V  L  Q  S  S  G  L  Y  S  L  S  S  V  V  T

1499 TGCCCTCCAGCAGCTTGGGCACCCAGACCTACATCTGCAACGTGAATCACAAGCCCAGCAACACCAAGGTGGACAAGAAA
        V  P  S  S  S  L  G  T  Q  T  Y  I  C  N  V  N  H  K  P  S  N  T  K  V  D  K  K

1579 GTTGGTGAGAGGCCAGCACAGGCAGGGAGGGTGTCTGCTGGAAGCCACGCTCAGCGCTCCTGCCTGGACGCATCCCGGCT
```

-continued

```
                                V
1659 ATGCAGCCCCAGTCCAGGCCAGCAACGCAGGCCCCGTCTGCCTCTTCACCCGGAGGCCTCTGCCCGCCCCACTCATGCTC

1739 AGGGAGAGGGTCTTCTGGCTTTTTCCCCAGGCTCTCGGCAGGCACAGGCTAGGTGCCCCTAACCCAGGCCCTGCACACAA

1819 AGGGGCAGGTGCTGGGCTCAGACCTGCCAAGAGCCATATCCCGGAGGACCCTGCCCCTGACCTAAGCCCACCCCAAAGGC

1899 CAAACTCTCCACTCCCTCAGCTCGGACACCTTCTCTCCTCCCAGATTCCAGTAACTCCCAATCTTCTCTCTGCAGAGCCC
                                                                                E  P
1979 AAATCTTGTGACAAAACTCACACATGCCCACCGTGCCCAGGTAAGCCAGCCCAGGCCTCGCCCTCCAGCTCAAGGCCGGA
        K  S  C  D  K  T  H  T  C  P  P  C  P
2059 CAGGTGCCCTAGAGTAGCCTGCATCCAGGGACAGGCCCCAGCCGGGTGCTGACACGTCCACCTCCATCTCTTCCTCAGCA
                                                                                   A
2139 CCTGAACTCCTGGGGGGACCGTCAGTCTTCCTCTTCCCCCCAAAACCCAAGGACACCCTCATGATCTCCCGGACCCCTGA
        P  E  L  L  G  G  P  S  V  F  L  F  P  P  K  P  K  D  T  L  M  I  S  R  T  P  E
2219 GGTCACATGCGTGGTGGTGGACGTGAGCCACGAAGACCCTGAGGTCAAGTTCAACTGGTACGTGGACGGCGTGGAGGTGC
        V  T  C  V  V  V  D  V  S  H  E  D  P  E  V  K  F  N  W  Y  V  D  G  V  E  V
2299 ATAATGCCAAGACAAAGCCGCGGGAGGAGCAGTACAACAGCACGTACCGTGTGGTCAGCGTCCTCACCGTCCTGCACCAG
        H  N  A  K  T  K  P  R  E  E  Q  Y  N  S  T  Y  R  V  V  S  V  L  T  V  L  H  Q
2379 GACTGGCTGAATGGCAAGGAGTACAAGTGCAAGGTCTCCAACAAAGCCCTCCCAGCCCCCATCGAGAAAACCATCTCCAA
        D  W  L  N  G  K  E  Y  K  C  K  V  S  N  K  A  L  P  A  P  I  E  K  T  I  S  K
2459 AGCCAAAGGTGGGACCCGTGGGGTGCGAGGGCCACATGGACAGAGGCCGGCTCGGCCCACCCTCTGCCCTGAGAGTGACC
        A  K
2539 GCTGTACCAACCTCTGTCCCTACAGGGCAGCCCCGAGAACCACAGGTGTACACCCTGCCCCCATCCCGGGATGAGCTGAC
                               G  Q  P  R  E  P  Q  V  Y  T  L  P  P  S  R  D  E  L  T
2619 CAAGAACCAGGTCAGCCTGACCTGCCTGGTCAAAGGCTTCTATCCCAGCGACATCGCCGTGGAGTGGGAGAGCAATGGGC
        K  N  Q  V  S  L  T  C  L  V  K  G  F  Y  P  S  D  I  A  V  E  W  E  S  N  G
2699 AGCCGGAGAACAACTACAAGACCACGCCTCCCGTGCTGGACTCCGACGGCTCCTTCTTCCTCTACAGCAAGCTCACCGTG
        Q  P  E  N  N  Y  K  T  T  P  P  V  L  D  S  D  G  S  F  F  L  Y  S  K  L  T  V
2779 GACAAGAGCAGGTGGCAGCAGGGGAACGTCTTCTCATGCTCCGTGATGCATGAGGCTCTGCACAACCACTACACGCAGAA
        D  K  S  R  W  Q  Q  G  N  V  F  S  C  S  V  M  H  E  A  L  H  N  H  Y  T  Q  K
2859 GAGCCTCTCCCTGTCTCCGGGTAAATGAGTGCGACGGCCGGCAAGCCCCGCTCCCCGGGCTCTCGCGGTCGCACGAGGA
        S  L  S  L  S  P  G  K  .
2939 TGCTTGGCACGTACCCCCTGTACATACTTCCCGGGCGCCCAGCATGGAAATAAAGCACCCAGCGCTGCCCTGGGCCCCTG

3019 CGAGACTGTGATGGTTCTTTCCACGGGTCAGGCCGAGTCTGAGGCCTGAGTGGCATGAGGGAGGCAGAGCGGGTCCCACT

3099 GTCCCCACACTGGCCCAGGCTGTGCAGGTGTGCCTGGGCCGCCTAGGGTGGGGCTCAGCCAGGGGCTGCCCTCGGCAGGG

3179 TGGGGGATTTGCCAGCGTGGCCCTCCCTCCAGCAGCACCTGCCCTGGGCTGGGCCACGGGAAGCCCTAGGAGCCCCTGGG

3259 GACAGACACACAGCCCCTGCCTCTGTAGGAGACTGTCCTGTTCTGTGAGCGCCCTGTCCTCCGACCTCCATGCCCACTCG

3339 GGGGCATGCCTAGTCCATGTGCGTAGGACAGGCCCTCCCTCACCCATCTACCCCCACGGCACTAACCCCTGGGCTGCCCT

3419 GCCCAGCCTCGCACCCGCATGGGGACACAACCGACTCCGGGGACATGCACTCTCGGGCCCTGTGGAGGGACTGGTGCAGA

3499 TGCCCACACACACACTCAGCCCAGACCCGTTCAACAAACCCCGCACTGAGGTTGGCCGGCCACACGGCCACCACACACAC

3579 ACGTGCACGCCTCACACACGGAGCCTCACCCGGGCGAACTGCACAGCACCCAGACCAGAGCAAGGTCCTCGCACACGTGA

3659 ACACTCCTCGGACACAGGCCCCCCACGAGCCCCACGCGGACCTCAAGGCCCACGAGCCTCTCGGCAGCTTCTCCACATGC
```

```
-continued
3739 TGACCTGCTCAGACAAACCCAGCCCTCCTCTCACAAGGGTGCCCCTGCAGCCGCCACACACACAGGGGATCACACACC

3819 ACGTCACGTCCCTGGCCCTGGCCCACTTCCCAGTGCCGCCCTTCCCTGCAGGATCC
```

Human constant region DNA sequences can be isolated in accordance with well known procedures from a variety of human cells, but preferably from immortalized B-cells. Suitable source cells for the polynucleotide sequences and host cells for immunoglobulin expression and secretion can be obtained from a number of sources well-known in the art.

In addition to the humanized immunoglobulins specifically described herein, other "substantially homologous" modified immunoglobulins can be readily designed and manufactured utilizing various recombinant DNA techniques well known to those skilled in the art. For example, the framework regions can vary from the native sequences at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis.

Alternatively, polypeptide fragments comprising only a portion of the primary antibody structure may be produced, which fragments possess one or more immunoglobulin activities (e.g., complement fixation activity). These polypeptide fragments may be produced by proteolytic cleavage of intact antibodies by methods well known in the art, or by inserting stop codons at the desired locations in vectors using site-directed mutagenesis, such as after CH1 to produce Fab fragments or after the hinge region to produce $F(ab')_2$ fragments. Single chain antibodies may be produced by joining VL and VH with a DNA linker.

As stated previously, the polynucleotides will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences.

*E. coli* is a prokaryotic host useful particularly for cloning the polynucleotides of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any of a number of well-known promoters may be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. Saccaromyces is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention. Eukaryotic cells are actually preferred, because a number of suitable host cell lines capable of secreting intact immunoglobulins have been developed in the art, and include the CHO cell lines, various COS cell lines, Syrian Hamster Ovary cell lines, HeLa cells, preferably myeloma cell lines, transformed B-cells, human embryonic kidney cell lines, or hybridomas. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, cytomegalovirus and the like.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Once expressed, the antibodies can be purified according to standard procedures, including ammonium sulfate precipitation, ion exchange, affinity, reverse phase, hydrophobic interaction column chromatography, gel electrophoresis, and the like. Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically or prophylactically, as directed herein.

The antibodies (including immunologically reactive fragments) are administered to a subject at risk for or exhibiting Aβ-related symptoms or pathology such as clinical or preclinical Alzheimer's disease, Down's syndrome, or clinical or pre-clinical amyloid angiopathy, using standard administration techniques, preferably peripherally (i.e. not by administration into the central nervous system) by intravenous, intraperitoneal, subcutaneous, pulmonary, transdermal, intramuscular, intranasal, buccal, sublingual, or suppository administration. Although the antibodies may be administered directly into the ventricular system, spinal fluid, or brain parenchyma, and techniques for addressing these locations are well known in the art, it is not necessary to utilize these more difficult procedures. The antibodies of the invention are effective when administered by the more simple techniques that rely on the peripheral circulation system. The advantages of the present invention include the ability of the antibody to exert its beneficial effects even though not provided directly to the central nervous system itself. Indeed, it has been demonstrated that the amount of antibody that crosses the blood-brain barrier is ≦0.1% of plasma levels.

The pharmaceutical compositions for administration are designed to be appropriate for the selected mode of administration, and pharmaceutically acceptable excipients such as, buffers, surfactants, preservatives, solubilizing agents, isotonicity agents, stabilizing agents and the like are used as appropriate. *Remington's Pharmaceutical Sciences*, Mack Publishing Co., Easton Pa., latest edition, incorporated herein by reference, provides a compendium of formulation techniques as are generally known to practitioners.

The concentration of the humanized antibody in formulations may range from as low as about 0.1% to as much as 15 or 20% by weight and will be selected primarily based on fluid volumes, viscosities, and so forth, in accordance with the particular mode of administration selected. Thus, a pharmaceutical composition for injection could be made up to contain in 1 mL of phosphate buffered saline from 1 to 100 mg of the humanized antibody of the present invention. The formulation could be sterile filtered after making the formulation, or otherwise made microbiologically acceptable. A typical composition for intravenous infusion could have a volume as much as 250 mL of fluid, such as sterile Ringer's solution, and 1-100 mg per mL, or more in antibody concentration. Therapeutic agents of the invention can be frozen or lyophilized for storage and reconstituted in a suitable sterile carrier prior to use. Lyophilization and reconstitution can lead to varying degrees of antibody activity loss (e.g. with conventional immune globulins, IgM antibodies tend to have greater activity loss than IgG antibodies). Dosages may have to be adjusted to compensate. The pH of the formulation will be selected to balance antibody stability (chemical and physical) and comfort to the patient when administered. Generally, pH between 4 and 8 is tolerated.

Although the foregoing methods appear the most convenient and most appropriate for administration of proteins such as humanized antibodies, by suitable adaptation, other techniques for administration, such as transdermal administration and oral administration may be employed provided proper formulation is designed.

In addition, it may be desirable to employ controlled release formulations using biodegradable films and matrices, or osmotic mini-pumps, or delivery systems based on dextran beads, alginate, or collagen.

In summary, formulations are available for administering the antibodies of the invention and are well-known in the art and may be chosen from a variety of options.

Typical dosage levels can be optimized using standard clinical techniques and will be dependent on the mode of administration and the condition of the patient.

The following examples are intended to illustrate but not to limit the invention.

The examples hereinbelow employ, among others, a murine monoclonal antibody designated "10D5" which was originally prepared by immunization with a peptide composed of residues 1-28 of human Aβ peptide. As the examples here describe experiments conducted in murine systems, the use of murine monoclonal antibodies is satisfactory. However, in the treatment methods of the invention intended for human use, humanized forms of the antibodies with the immunospecificity corresponding to that of antibody 10D5 are preferred.

EXAMPLE 1

Synthesis of Humanized Antibody 10D5

Cells and Antibodies.

Mouse myeloma cell line Sp2/0 was obtained from ATCC (Manassas, Va.) and maintained in DME medium containing 10% FBS (Cat # SH30071.03, HyClone, Logan, UT) in a 37° C. $CO_2$ incubator. Mouse 10D5 hybridoma cells were first grown in RPMI-1640 medium containing 10% FBS (HyClone), 10 mM HEPES, 2 mM glutamine, 0.1 mM non-essential amino acids, 1 mM sodium pyruvate, 25 μg/ml gentamicin, and then expanded in serum-free media (Hybridoma SFM, Cat # 12045-076, Life Technologies, Rockville, Md.) containing 2% low Ig FBS (Cat # 30151.03, HyClone) to a 1.5 liter volume in roller bottles. Mouse monoclonal antibody 10D5 (Mu10D5) was purified from the culture supernatant by affinity chromatography using a protein-G Sepharose column. Biotinylated Mu10D5 was prepared using EZ-Link Sulfo-NHS-LC-LC-Biotin (Cat # 21338ZZ, Pierce, Rockford, Ill.).

Cloning of Variable Region cDNAs.

Total RNA was extracted from approximately $10^7$ hybridoma cells using TRIzol reagent (Cat. # 15596-026, Life Technologies) and poly(A)$^+$RNA was isolated with the PolyATract mRNA Isolation System (Cat. # Z5310, Promega, Madison, Wis.) according to the suppliers' protocols. Double-stranded cDNA was synthesized using the SMART™RACE cDNA Amplification Kit (Cat. # K1811-1, Clontech, Palo Alto, Calif.) following the supplier's protocol. The variable region cDNAs for the light and heavy chains were amplified by polymerase chain reaction (PCR) using 3' primers that anneal respectively to the mouse kappa and gamma chain constant regions, and a 5' universal primer provided in the SMART™RACE cDNA Amplification Kit. For VL PCR, the 3' primer has the sequence:

```
                                              [SEQ ID NO:13]
5'-TATAGAGCTCAAGCTTGGATGGTGGGAAGATGGATACAGTTGGTGC-
3'
``` with residues 17-46 hybridizing to the mouse Ck region. For VH PCR, the 3' primers have the degenerate sequences:

```
                                    A    G    T
5'-TATAGAGCTCAAGCTTCCAGTGGATAGACCGATGGGGCTGTCGTTTTGGC-3'   [SEQ ID NO:14]
                                         T
``` with residues 17-50 hybridizing to mouse gamma chain CH1. The VL and VH cDNAs were subcloned into pCR4Blunt-TOPO vector (Cat. # 45-0031, Invitrogen, Carlsbad, Calif.) for sequence determination. DNA sequencing was carried out by PCR cycle sequencing reactions with fluorescent dideoxy chain terminators (Applied Biosystems, Foster City, Calif.) according to the manufacturer's instructions. The sequencing reactions were analyzed on a Model 377 DNA Sequencer (Applied Biosystems).

Construction of Humanized 10D5 (Hu10D5) Variable Regions.

Humanization of the mouse antibody V regions was carried out as outlined by Queen et al., 1989, op. Cit. The human V region framework used as acceptor for Mu10D5 CDRs was chosen based on sequence homology. The computer programs ABMOD and ENCAD [Levitt, M., J. Mol. Biol. 168:595-620 (1983)] were used to construct a molecular model of the variable regions. Amino acids in the humanized V regions that were predicted to have contact with CDRs were substituted with the corresponding residues of Mu10D5. This was done at residue 98 in the heavy chain and at residues 41 and 51 in the light chain. The amino acids in the humanized V region that were found to be rare in the same V-region subgroup were changed to the consensus amino acids to eliminate potential immunogenicity. This was done at residues 42 and 44 in the light chain and at residue 24 in the heavy chain.

The light and heavy chain variable region genes were constructed and amplified using eight overlapping synthetic oligonucleotides ranging in length from approximately 65 to 80 bases [He, X. Y., et al., J. Immunol. 160: 1029-1035 (1998)]. The oligonucleotides were annealed pairwise and extended with the Klenow fragment of DNA polymerase I, yielding four double-stranded fragments. The resulting fragments were denatured, annealed pairwise, and extended with Klenow, yielding two fragments. These fragments were denatured, annealed pairwise, and extended once again, yielding a full-length gene. The resulting product was amplified by PCR using the Expand High Fidelity PCR System (Cat. # 1 732 650, Roche Molecular Biochemicals, Indianapolis, Ind.). The PCR-amplified fragments were gel-purified and cloned into pCR4Blunt-TOPO vector. After sequence confirmation, the VL and VH genes were digested with MluI and XbaI, gel-purified, and subcloned respectively into vectors for expression of light and heavy chains to make pVk-Hu10D5 and pVg1-Hu10D5 [Co, M. S., et al., J. Immunol. 148:1149-1154 (1992)]. The mature humanized 10D5 antibody expressed from these plasmids has the light chain of SEQ ID NO:11 and the heavy chain of SEQ ID NO:12.

Stable Transfection.

Stable transfection into mouse myeloma cell line Sp2/0 was accomplished by electroporation using a Gene Pulser apparatus (BioRad, Hercules, Calif.) at 360 V and 25 μF as described (Co, et al., 1992, op. cit.). Before transfection, pVk-Hu10D5 and pVg1-Hu10D5 plasmid DNAs were linearized using FspI. Approximately $10^7$ Sp2/0 cells were transfected with 20 μg of pVk-Hu 10D5 and 40 μg of pVg1-Hu10D5. The transfected cells were suspended in DME medium containing 10% FBS and plated into several 96-well plates. After 48 hr, selection media (DME medium containing 10% FBS, HT media supplement, 0.3 mg/ml xanthine and 1 μg/ml mycophenolic acid) was applied. Approximately 10 days after the initiation of the selection, culture supernatants were assayed for antibody production by ELISA as shown below. High yielding clones were expanded in DME medium containing 10% FBS and further analyzed for antibody expression. Selected clones were then adapted to growth in Hybridoma SFM.

Measurement of Antibody Expression by ELISA.

Wells of a 96-well ELISA plate (Nunc-Immuno plate, Cat # 439454, NalgeNunc, Naperville, Ill.) were coated with 100 μl of 1 μg/ml goat anti-human IgG, Fc γ fragment specific, polyclonal antibodies (Cat. # 109-005-098, Jackson ImmunoResearch, West Grove, Pa.) in 0.2 M sodium carbonate-bicarbonate buffer (pH 9.4) overnight at 4° C. After washing with Washing Buffer (PBS containing 0.1% Tween 20), wells were blocked with 400 μl of Superblock Blocking Buffer (Cat # 37535, Pierce) for 30 min and then washed with Washing Buffer. Samples containing Hu10D5 were appropriately diluted in ELISA Buffer (PBS containing 1% BSA and 0.1% Tween 20) and applied to ELISA plates (100 μl per well). As a standard, humanized anti-CD33 IgG1 monoclonal antibody HuM195 (Co, et al., 1992, op. cit.) was used. The ELISA plate was incubated for 2 hr at room temperature and the wells were washed with Washing Buffer. Then, 100 μl of 1/1,000-diluted HRP-conjugated goat anti-human kappa polyclonal antibodies (Cat # 1050-05, Southern Biotechnology, Birmingham, Al.) in ELISA Buffer was applied to each well. After incubating for 1 hr at room temperature and washing with Washing Buffer, 100 μl of ABTS substrate (Cat #s 507602 and 506502, Kirkegaard and Perry Laboratories, Gaithersburg, Md.) was added to each well. Color development was stopped by adding 100 μl of 2% oxalic acid per well. Absorbance was read at 415 nm using an OPTImax microplate reader (Molecular Devices, Menlo Park, Calif.).

Purification of Hu10D5.

One of the high Hu10D5-expressing Sp2/0 stable transfectants (clone #1) was adapted to growth in Hybridoma SFM and expanded to 2 liters in roller bottles. Spent culture supernatant was harvested when cell viability reached 10% or below and loaded onto a protein-A Sepharose column. The column was washed with PBS before the antibody was eluted with 0.1 M glycine-HCl (pH 2.8), 0.1 M NaCl. The eluted protein was dialyzed against 3 changes of 2 liters of PBS and filtered through a 0.2 μm filter prior to storage at 4° C. Antibody concentration was determined by measuring absorbance at 280 nm (1 mg/ml=1.4 $A_{280}$). SDS-PAGE in Tris-glycine buffer was performed according to standard procedures on a 4-20% gradient gel (Cat # EC6025, Novex, San Diego, Calif.). Purified humanized 10D5 antibody is reduced and run on an SDS-PAGE gel. The whole antibody shows two bands of approximate molecular weights 25 kDa and 50 kDa. These results are consistent with the molecular weights of the light chain and heavy chain, or with the molecular weight of the chain(s) comprising a fragment, calculated from their amino acid compositions.

EXAMPLE 2

In Vitro Binding Properties of Humanized 10D5 Antibody

The binding efficacy of humanized 10D5 antibody, synthesized and purified as described above, was compared with the mouse 10D5 antibody using biotinylated mouse 10D5 antibody in a comparative ELISA. Wells of a 96-well ELISA plate (Nunc-Inmuno plate, Cat # 439454, Nalge-Nunc) were coated with 100 μl of β-amyloid peptide (1-42) in 0.2 M sodium carbonate/bicarbonate buffer (pH 9.4) (1 μg/mL) overnight at 4° C.

After washing the wells with phosphate buffered saline (PBS) containing 0.1% Tween 20 (Washing Buffer) using an ELISA plate washer, the wells were blocked by adding 300 μL of SuperBlock reagent (Pierce) per well. After 30 minutes of blocking, the wells were washed with Washing Buffer and excess liquid was removed.

A mixture of biotinylated Mu10D5 (0.4 μg/ml final concentration) and competitor antibody (Mu10D5 or Hu10D5; starting at 1000 μg/ml final concentration and serial 3-fold dilutions) in ELISA Buffer were added in triplicate in a final volume of 100 μl per well. As a no-competitor control, 100 μl of 0.4 μg/ml biotinylated Mu10D5 was added. As a background control, 100 μl of ELISA Buffer was added. The ELISA plate was incubated at room temperature for 90 min. After washing the wells with Washing Buffer, 100 µl of µg/ml HRP-conjugated streptavidin (Cat # 21124, Pierce) was added to each well. The plate was incubated at room temperature for 30 min and washed with Washing Buffer. For color development, 100 µl/well of ABTS Peroxidase Substrate (Kirkegaard & Perry Laboratories) was added. Color development was stopped by adding 100 µl/well of 2% oxalic acid. Absorbance was read at 415 nm. The absorbances were plotted against the log of the competitor concentration, curves were fit to the data points (using Prism) and the IC50 was determined for each antibody using methods well-known in the art.

The mean IC50 for mouse 10D5 was 23.4 µg/mL (three separate experiments, standard deviation=5.5 µg/mL) and for humanized 10D5 was 49.1 µg/mL (three separate experiments, standard deviation=11.8 µg/mL). A second set of three experiments was carried out, essentially as described above, and the mean IC50 for mouse 10D5 was determined to be 20 µg/mL (SD=1 µg/mL) and for humanized 10D5, the IC50 was determined to be 16 µg/mL (SD=0.6 µg/mL). On the basis of these results, we conclude that humanized 10D5 has binding properties that are very similar to those of the mouse antibody 10D5. Therefore, we expect that humanized 10D5 has very similar in vitro and in vivo activities compared with mouse 10D5 and will exhibit in humans the same effects demonstrated with mouse 10D5 in mice.

EXAMPLE 3

In Vitro Binding Properties of Mouse and Humanized Antibodies 10D5

Antibody affinity (KD=Kd/Ka) was determined using a BIAcore biosensor 2000 and data analyzed with BIAevaluation (v. 3.1) software. A capture antibody (rabbit anti-mouse Ig or anti-human Ig) was coupled via free amine groups to carboxyl groups on flow cell 2 of a biosensor chip (CM5) using N-ethyl-N-dimethylaminopropyl carbodiimide and N-hydroxysuccinimide (EDC/NHS). A non-specific rabbit IgG was coupled to flow cell 1 as a background control. Monoclonal antibodies were captured to yield 300 resonance units (RU). Amyloid-beta 1-40 or 1-42 (Biosource International, Inc.) was then flowed over the chip at decreasing concentrations (1000 to 0.1 times KD). To regenerate the chip, bound anti-Aβ antibody was eluted from the chip using a wash with glycine-HCl (pH 2). A control injection containing no amyloid-beta served as a control for baseline subtraction. Sensorgrams demonstrating association and dissociation phases were analyzed to determine Kd and Ka. The affinity (KD) of mouse antibody 10D5 for Aβ 1-40 was determined to be 390 nM, and the affinity of humanized 10D5, prepared essentially as described in Example 1, was determined to be 209 nM. Affinity for Aβ 1-42 was biphasic for both mouse 10D5 and humanized 10D5. For mouse 10D5, the affinities for Aβ 1-42 were 0.57 nM and 4950 nM. Humanized 10 D5 had affinities for Aβ 1-42 of 0.19 nM and 1020 nM.

EXAMPLE 4

Epitope Mapping of Mouse and Humanized 10D5

The BIAcore is an automated biosensor system for measuring molecular interactions [Karlsson R., et al. *J. Immunol. Methods* 145:229-240 (1991)]. The advantage of the BIAcore over other binding assays is that binding of the antigen can be measured without having to label or immobilize the antigen (i.e. the antigen maintains a more native conformation). The BIAcore methodology was used to assess the binding of various amyloid-beta peptide fragments to either mouse 10D5 or humanized 10D5 (prepared substantially as described in Example 1). All dilutions were made with HEPES buffered saline containing Tween 20. A single concentration of a variety of fragments of human Aβ or mouse Aβ 1-40 (BioSource International) was used. Human amyloid beta fragments 1-10 and 1-20 bound to mouse 10D5 and to humanized 10D5, while human Aβ fragments 10-20 and 16-25 did not bind to either antibody. Neither mouse 10D5 nor humanized 10D5 bound mouse Aβ 1-40. Using this methodology, the binding epitope for both mouse and humanized 10D5 appears to be between amino acids 1 and 10 of human Aβ.

EXAMPLE 5

In Vivo Experiments with 10D5

Unless otherwise stated, all studies used PDAPP mice, and all injections were intraperitoneal (i.p.) In general, a control group of mice received injections of saline. In some cases, another control group received injections of a non-specific mouse IgG preparation.

Six weeks of weekly injection of 360 µg of 10D5 in old mice (24 month) raised soluble $A\beta_{total}$ in hippocampus by 16% and Aβ 1-42 in hippocampus by 21%, while lowering hippocampal insoluble $A\beta_{total}$ by 24% and Aβ 1-42 by 26% (no statistically significant difference; 9 animals per control group and 10 animals per antibody group). In the cortex, mean insoluble $A\beta_{total}$ was lower by 27% and Aβ 1-42 by 29%, while mean insoluble Aβ 1-40 increased by 7% (no statistically significant differences).

In hemizygous, 4 month old mice, administration of 360 µg 10D5 per animal: 1) raised average plasma Aβ 1-40 and Aβ 1-42 levels approximately 3-fold by 24 hours after administration; and 2) had no significant effect on soluble Aβ 1-40 in the cortex after 24 hours compared with saline control (no differences were statistically significant; 5 animals per group).

Administration of 360 µg of 10DS per animal (5 animals per group, saline control): 1) raised average plasma Aβ 1-40 and Aβ 1-42 levels approximately 14-fold and 19-fold, respectively by 24 hours after administration; 2) had no consistent or significant effect on soluble or insoluble Aβ 1-40, Aβ 1-42, or $A\beta_{total}$ in the cortex or hippocampus after 24 hours; 3) lowered soluble Aβ 1-40, Aβ 1-42, and $A\beta_{total}$ in the cerebellum by 50% ($p<0.05$), 33%, and 13%, respectively; and 4) lowered insoluble Aβ 1-40, Aβ 1-42, and $A\beta_{total}$ the cerebellum by 53% ($p<0.001$), 46% ($p<0.001$), and 30% ($p<0.01$), respectively.

In young mice, administration of 360 µg of 10D5 per animal (5 per group): 1) raised average plasma Aβ 1-42 levels approximately 33% by 24 hours after administration; and 2) in the cortex, raised soluble Aβ 1-40 3.4-fold ($p<0.001$), lowered soluble Aβ 1-42 by 22% ($p<0.05$), lowered insoluble AP 1-40 about 10% and increased insoluble AP 1-42 about 12%.

We claim:

1. An antibody comprising a light chain variable region comprising SEQ ID NO:9 and a heavy chain variable region comprising SEQ ID NO:10.

2. A polynucleotide compound, comprising a sequence coding for either SEQ ID NO:9 or SEQ ID NO:10 of the antibody of claim 1.

3. A cell culture wherein the cultured cells express the antibody of claim 1.

4. A pharmaceutical composition, comprising the antibody of claim 1 and a pharmaceutically acceptable excipient.

5. A method for increasing plasma Aβ levels or reducing brain Aβ plaque burden in a human subject diagnosed with Alzheimer's disease, comprising administering to the human subject an effective amount of the antibody of claim 1.

6. An antibody comprising a light chain variable region comprising SEQ ID NO:11 and a heavy chain variable region comprising SEQ ID NO:12.

7. polynucleotide compound, comprising a sequence coding for either SEQ ID NO:11 or SEQ ID NO:12 of the antibody of claim 6.

8. A cell culture wherein the cultured cells express the antibody of claim 6.

9. A pharmaceutical composition, comprising the antibody of claim 6 and a pharmaceutically acceptable excipient.

10. A method for increasing plasma Aβ levels or reducing brain Aβ plague burden in a human subject diagnosed with Alzheimer's disease, comprising administering to the human subject an effective amount of the antibody of claim 6.

11. An antibody fragment comprising a light chain variable region sequence comprising SEQ ID NO:9 and a heavy chain variable region sequence comprising SEQ ID NO:10.

12. The antibody fragment of claim 11, wherein the antibody fragment is a Fab or a F(ab')2 fragment.

13. The antibody fragment of claim 11, wherein the antibody fragment is a single chain.

14. A polynucleotide compound, comprising a sequence coding for either SEQ ID NO:9 or SEQ ID NO:10 of the antibody fragment of claim 11.

15. A cell culture wherein the cultured cells express the antibody of claim 11.

16. A pharmaceutical composition, comprising the antibody fragment of claim 11 and a pharmaceutically acceptable excipient.

17. A method for increasing plasma Aβ levels or reducing brain Aβ plaque burden in a human subject diagnosed with Alzheimer's disease, comprising administering to the human subject an effective amount of the antibody of claim 11.

* * * * *